US012060413B2

(12) United States Patent
Blanchetot et al.

(10) Patent No.: US 12,060,413 B2
(45) Date of Patent: Aug. 13, 2024

(54) METHOD OF PREPARING pH-DEPENDENT ANTIBODIES

(71) Applicant: argenx BV, Ghent (BE)

(72) Inventors: Christophe Blanchetot, Ghent (BE); Erik Hofman, Ghent (BE); Johannes De Haard, Ghent (BE); Jacobus Cornelis Rasser, Ghent (BE)

(73) Assignee: argenx BV, Ghent (BE)

( * ) Notice: Subject to any disclaimer, the term of this patent is extended or adjusted under 35 U.S.C. 154(b) by 708 days.

(21) Appl. No.: 16/606,656

(22) PCT Filed: May 10, 2018

(86) PCT No.: PCT/EP2018/062179
§ 371 (c)(1),
(2) Date: Oct. 18, 2019

(87) PCT Pub. No.: WO2018/206748
PCT Pub. Date: Nov. 15, 2018

(65) Prior Publication Data
US 2022/0177555 A1 Jun. 9, 2022

(30) Foreign Application Priority Data
May 10, 2017 (GB) .................... 1707484

(51) Int. Cl.
*C07K 16/18* (2006.01)
*C07K 16/00* (2006.01)

(52) U.S. Cl.
CPC .............. *C07K 16/18* (2013.01); *C07K 16/00* (2013.01); *C07K 2317/22* (2013.01); *C07K 2317/55* (2013.01); *C07K 2317/565* (2013.01); *C07K 2317/567* (2013.01); *C07K 2317/92* (2013.01); *C07K 2317/94* (2013.01); *G01N 2500/04* (2013.01)

(58) Field of Classification Search
None
See application file for complete search history.

(56) References Cited

FOREIGN PATENT DOCUMENTS

| | | | |
|---|---|---|---|
| EP | 2275443 | A1 | 1/2011 |
| JP | 201221004 | A | 2/2012 |
| WO | WO 2013/138680 | A1 | 9/2013 |
| WO | WO 2014/028354 | A1 | 2/2014 |
| WO | 2016000813 | A1 | 1/2016 |

OTHER PUBLICATIONS

Schroter et al. 'A generic approach to engineer antibody pHswitches using combinatorial histidine scanning libraries and yeast display.' mAbs 7:1, 138-151; Jan./Feb. 2015. Published online Dec. 18, 2014. doi: 10.4161/19420862.2014.985993.*
Igawa, "Antibody recycling by engineered pH-dependent antigen binding improves the duration of antigen neutralization", Nature Biotechnology, vol. 28, No. 11, pp. 1203-1207, Nov. 28, 2011 doi: 10.1038/nbt.1691.
International Search Report and Written Opinion in related PCT Application No. PCT/EP2018/062179, mailed Aug. 13, 2018 (18 pages).
Ippolito et al., "Forced usage of positively charged amino acids in immunoglobulin CDR-H3 impairs B cell development and antibody production", The Journal of Experimental Medicine, vol. 203, No. 6, pp. 1657-1578, Jun. 12, 2006 doi: 10.1084/jem.20052217.
Ito et al., "The His-probe method: effects of histidine residues introduced into the complementarity-determining regions of antibodies on antigen-antibody interactions at different pH values", FEBS Lett, Elsevier, vol. 309, No. 1, pp. 85-88, Aug. 1, 1992.
Murtaugh et al., "A combinatorial histidine scanning library approach to engineer highly pH-dependent protein switched", Protein Science, vol. 20, No. 9, pp. 1619-1631, 2011 doi: 10.1002/pro.696.
Shi et al., "Comparative analysis of human and mouse immunoglobulin variable heavy regions from IMGT/LIGM-DB with IMGT/HighV-QUEST", Theoretical Biology and Medical Modelling, vol. 11, No. 1, p. 30, Jan. 1, 2014 doi: 10.1186/1742-4682-11-30.
Strauch et al., Computational design of a pH-sensitive IgG binding protein, Proceedings of the National Academy of Sciences USA, vol. 111, No. 2, pp. 675-680, Dec. 31, 2013 doi: 10.1073/pnas.1313605111.
Declaration of Christophe Blanchetot, Mar. 16, 2021.

* cited by examiner

*Primary Examiner* — Nora M Rooney
(74) *Attorney, Agent, or Firm* — Dechert LLP; Andrew T. Wilkins

(57) ABSTRACT

Methods for preparing engineered antibodies exhibiting improved pH-dependent antigen binding are disclosed. The methods are based on introduction of histidine residues at a subset of defined amino acid positions within the antibody CDRs. The set of amino acid positions selected for histidine substitution is derived from a heat-map of histidine occurrence within the CDRs of functional antibodies from a natural antibody repertoire. The methods provide a simpler and less time-consuming approach to the identification of pH-dependent antibody variants.

33 Claims, 4 Drawing Sheets

METHOD OF PREPARING pH-DEPENDENT ANTIBODIES

RELATED APPLICATIONS

This application is a 35 U.S.C. § 371 filing of International Patent Application No. PCT/EP2018/062179, filed May 10, 2018, which claims priority to Great Britain Patent Application No. 1707484.0, filed May 10, 2017, the entire disclosures of which are hereby incorporated herein by reference in their entirety.

FIELD OF THE INVENTION

The present disclosure relates to the field of antibody engineering, and in particular to methods for engineering antibody variants exhibiting pH-dependent binding to a target antigen, as well as to antibodies prepared by the methods.

BACKGROUND

There is growing interest in the engineering of antibodies that exhibit pH-dependent binding to a target antigen. In particular, it is of interest to identify antibodies that exhibit reduced antigen binding at acidic pH, as compared to neutral pH.

Incorporation of pH-sensitive antigen binding can result in improved function of engineered antibodies in vivo. Antibodies may be engineered to retain high affinity antigen binding at neutral pH (e.g. pH 7.4) and to show decreased binding at acidic pH (e.g. pH 4.5-6.0). When entering the endosomal pathway, pH-dependent antigen binding allows dissociation of the antibody-antigen complex in the acidified endosome (~pH 6.0) and FcRn-mediated recycling of free antibody, in turn promoting enhanced antigen clearance that may enable less frequent or lower antibody dosing.

Typically, pH-dependent antibody-antigen binding relies on the presence of ionizable histidine residues that mediate structural transitions in binding or folding of the interacting antibody. Alterations of electrostatic interactions that are induced upon histidine protonation at lower pH-values can lead to decreased binding affinity.

Various protein engineering approaches have been described that aim to incorporate pH-sensitivity into proteins by using different strategies of histidine substitution. For example, rational design guided by structural modelling of the receptor interaction site of granulocyte colony-stimulating factor (GCSF) allowed for the identification of mutational sites that upon histidine substitution lead to a pH-sensitive variant (Sarkar et al., Nat Biotechnol, Vol. 20, pp908-13, 2002). However, the assessment of individual positions for histidine substitutions that can mediate pH-sensitivity in proteins is time-consuming and unpredictable.

As an alternative approach, screening of combinatorial libraries with suitable high-throughput technologies, e.g. yeast surface display (YSD) or phage display, has been applied to the engineering of pH-sensitive binding in a variety of different protein scaffolds. Schröter et al., mAbs, vol. 7(1), 138-151, 2015 describe a generic strategy for the engineering of antibody heavy and light chain variable domains for reversible pH-sensitive antigen binding. This approach relies on the generation and screening of heavy and light chain combinatorial histidine substitution libraries. In this approach, histidine mutations are randomly introduced into the complementary-determining regions (CDRs) of the VH and VL regions. Histidine mutations may be introduced at any amino acid position in the CDRs of the VH domain and the VL domain. The rate of histidine mutation is adjusted to achieve on average three random mutations per library variant. The complete library therefore theoretically contains variants including all possible combinations of three random histidine substitutions in the CDRs.

This combinatorial library approach did allow the successful identification of engineered variants of adalimumab exhibiting pH-dependent binding to TNF. However, the strategy is relatively time consuming, owing to the large size of the library required to sample all amino acid positions within the CDRs of the VH and VL domains for possible histidine substitution. Furthermore, it does not take into account overall antibody structure and stability by introducing histidine residues at unfavourable positions.

SUMMARY OF THE INVENTION

There is a need for alternative methods for preparing engineered antibody variants exhibiting pH-dependent binding to a target antigen, which are simpler and less time-consuming to perform than prior art methods. Moreover, there is also a need for methods which enable identification of engineered antibodies that exhibit pH-dependent antigen-binding, without unduly affecting antigen-binding capability at neutral pH.

To address these needs, the applicant has performed a systematic analysis of the natural occurrence of histidine residues within the complementarity-determining regions (CDRs) of a large repertoire of functional (i.e. antigen-binding) antibody variable domains. The results of this analysis enabled the applicant to derive a "heat-map" of natural histidine occurrence within native antibodies. The "heat-map" provides both a list of "hot-spot" amino acid residues within the CDRs at which histidine may occur naturally within the antibody repertoire, and also a list of "cold-spot" amino acid residues in the CDRs at which histidine typically does not naturally occur. The "hot-spot" and "cold-spot" lists can be applied to the engineering of pH-dependent antibody variants for example in a rational design or a combinatorial approach.

In a first aspect the invention provides a method of preparing an engineered antibody exhibiting pH-dependent binding to its antigen, comprising preparing the engineered antibody by substituting at least one amino acid residue of a parental antibody with a histidine residue, wherein at least one amino acid residue selected from the following hot-spot list is substituted with histidine:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |

-continued

| | |
|---|---|
| VL CDR2 | L50, L51a, L51b, L51c, L51d, L56 |
| VL CDR3 | L95, L95d, L95e, L95f, L97 | wherein said engineered antibody exhibits pH-dependent binding to its antigen.

The engineered antibody exhibits improved pH-dependent binding (i.e. greater pH-dependence), as compared to the parental antibody, as a result of the histidine substitution(s).

The invention further provides a method of preparing an engineered antibody exhibiting pH-dependent binding to its antigen, comprising the steps of:

(a) providing a parental antibody which binds to an antigen;

(b) preparing a panel of engineered variants of said parental antibody, wherein each of said engineered variants in said panel differs from said parental antibody by substitution of at least one amino acid residue with a histidine residue, wherein at least one amino acid residue selected from the following hot-spot list is substituted with histidine:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 |

(c) screening said panel of engineered variants for pH dependent binding to said antigen and thereby identifying an engineered antibody exhibiting pH-dependent binding to said antigen.

The engineered antibody identified in step (c) exhibits improved pH-dependent binding (i.e. greater pH-dependence), as compared to the parental antibody, as a result of the histidine substitution(s).

The invention further provides method of preparing an engineered antibody exhibiting pH dependent binding to its antigen, comprising the steps of:

(a) identifying a parental antibody which binds to an antigen;

(b) preparing a panel of engineered variants of said parental antibody, wherein each of said engineered variants in said panel differs from said parental antibody by substitution of at least one amino acid residue with a histidine residue, wherein at least one amino acid residue selected from the following hot-spot list is substituted with histidine:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 |

(c) screening said panel of engineered variants for pH dependent binding to said target antigen and thereby identifying selected amino acid positions at which the presence of histidine confers pH dependent binding to said antigen;

(d) preparing one or more further engineered variants of said parental antibody, wherein each of said variants comprises histidine at two or more selected amino acid positions identified in step (c); and (e) screening said further engineered variants for pH dependent binding to said antigen; and thereby identifying an engineered antibody exhibiting pH dependent binding to said antigen.

The engineered antibody identified in step (e) exhibits improved pH-dependent binding (i.e. greater pH-dependence), as compared to the parental antibody, as a result of the histidine substitution(s).

In a second aspect the invention provides an engineered antibody exhibiting pH dependent binding to its antigen wherein at least one amino acid in the CDRs of the engineered antibody is a histidine residue, characterised in that at least one amino acid residue selected from the following hot-spot list is a histidine residue:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue selected from the following cold-spot list is not a histidine residue:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 |

DETAILED DESCRIPTION

The present disclosure provides methods of preparing engineered antibodies exhibiting pH-dependent binding to a target antigen, based on substitution of selected amino acids in the variable domains of a parental antibody (and preferentially within the CDRs thereof) with histidine residues. It is generally known in the art that introduction of ionizable histidine residues into the VH and/or VL domains of antibody molecules may alter pH-dependence of antigen binding. However, to date the available methods for engineering of pH-dependent antigen binding have largely relied upon screening of random combinatorial libraries in which all amino acid residues in the CDRs are sampled for possible replacement with histidine.

The present methods differ from those in the prior art in that the selection of particular amino acid residues for substitution with histidine is guided by the natural occurrence of histidine residues at specific amino acid positions within the VH and VL domains of functional antibody molecules, and more particularly within the CDRs thereof, and also by the natural absence of histidine residues at other amino acid positions in the CDRs. Accordingly, the methods disclosed herein are based on histidine substitution at amino acid positions chosen from a pre-selected subset of amino acid positions within the variable domains (and in particular the CDRs), whereas other residues in the CDRs are preselected as preferably not to be substituted with histidine.

The amino acid residues pre-selected as candidates for substitution with histidine are referred to herein as "hot-spot" residues (Table A). These are amino acid positions in the CDRs, or framework positions proximal to the CDRs, at which histidine has been observed to occur naturally within a functional antibody repertoire.

TABLE A (hot-spot residue positions)

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VLCDR3 | L89, L90, L91, L92, L93, L94, L95a, L95b, L95c, L96 |
| FR | L49, L87 |

The amino acid residues pre-selected as preferably not to be substituted with histidine are referred to herein as "cold-spot" residues (Table B). These are amino acid positions in the CDRs, or framework positions proximal to the CDRs, at which histidine has not been observed within a functional antibody repertoire.

TABLE B (cold-spot residue positions)

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 |

The present disclosure provides a method of preparing an engineered antibody exhibiting pH-dependent binding to its antigen, comprising preparing the engineered antibody by substituting at least one amino acid residue of a parental antibody with a histidine residue (which may be abbreviated herein to HIS). The engineered antibody exhibits improved pH-dependent binding (i.e. greater pH-dependence), as compared to the parental antibody, as a result of the histidine substitution(s). The "parental antibody" may be any antibody that is capable of binding to an antigen of interest. The parental antibody is typically a conventional four-chain immunoglobulin, in which antigen-binding specificity is conferred by paired VH and VL domains. However, the method is also applicable to engineering of pH-dependent binding in other parental antibodies, and antigen-binding fragments, such as to Fab, F(ab'), F(ab')$_2$, Fv, scFv, diabodies, triabodies, minibodies etc, and any other modified immunoglobulin configuration comprising an antigen binding site provided by paired VH and VL domains. In certain embodiments the parental antibody, or the variable domains or CDRs thereof, may be derived from a camelid species, including but not limited to llama, camel, dromedary, alpaca, vicuña or guanaco. Preparation of camelid monoclonal antibodies is described in detail in WO2010/001251, the contents of which are incorporated herein by reference. Other preferred features of the parental antibody, and the engineered antibody derived therefrom, are described elsewhere herein. The nature of the antigen to which the parental antibody binds is not particularly limited.

The engineered antibody is prepared by substitution of one or more selected amino acid residues of the parental antibody with histidine. The engineered antibody may include a total of 1, 2, 3, 4, 5, or more histidine substitutions as compared to the parental antibody. The selected amino acid residues substituted with histidine are typically located within the CDRs of the antibody variable domains, or at framework positions proximal to the CDRs. In the case of antibody molecules comprising paired VH and VL domains, the residues selected for substitution with histidine may be located in the CDRs of the VH domain, or in the CDRs of the VL domain or in the CDRs of both the VH domain and the VL domain.

As described herein, at least one of the amino acid positions substituted with histidine must be selected from the "hot-spot" list (Table A). In certain embodiments at least two, at least three, at least four, or at least five of the amino acid positions substituted with histidine are selected from the "hot spot" list. In certain embodiments, all of the histidine substitutions in the engineered antibody are made at amino acid positions selected from the hot-spot list (Table A), i.e. only residues in the hot-spot list may be selected for substitution with histidine. However, in other embodiments, histidine substitutions may be included at one or more positions that are not on the hot-spot list, provided that at least one of the histidine substitutions is made at a position selected from the hot-spot list (Table A). By way of example, as discussed below, in certain embodiments one or more histidine substitutions may be included at "cold-spot" positions within VH CDR3 and/or VL CDR3.

As described herein, there are certain amino acid positions in the parental antibody that are preferably not selected for substitution with histidine. These amino acid positions are those shown on the "cold-spot" list (Table B). The engineered antibodies prepared according to the methods described herein must include at least one amino acid position on the cold-spot list (Table B) which is not substituted with histidine. In certain embodiments, at least two, at least three, at least four, or at least five of the amino acid positions on the cold-spot list (Table B) are not substituted with histidine. In further embodiments, none of the amino acid positions on the cold-spot list (Table B) are substituted with histidine.

In the case of VH CDR3 and VL CDR3, it is permissible (and may be beneficial in certain embodiments) to introduce histidine substitutions also at one or more of the cold-spot amino acid residue positions listed in Table B, and test to resulting antibody variant(s) for pH-dependent binding. Given the highly variable nature of VH CDR3 and VL CDR3, the introduction of histidine residues at the cold-spot positions in these CDRs (in addition to or as an alternative to the hot-spot positions) may be more readily tolerated within the antibody structure than at the cold-spot positions in CDR1 and CDR2, and may make an important contribution to pH-dependent antigen binding. Accordingly, substitution of histidine at the listed cold-spot positions in VH CDR3 and VL CDR3 is permitted in all aspects of the invention.

In one specific embodiment all of the amino acid residues substituted with histidine are selected from the hot-spot list (Table A), with the proviso that one or more of the following residues may be additionally substituted with histidine: H100g, H100k, H100m, H100n, L95, L95d, L95e, L95f, L97.

pH-Dependent Binding

Engineered antibodies into which one or more histidine substitutions have been introduced in accordance with the methods described herein may exhibit pH-dependent binding to a target antigen.

As used herein in relation to antibody-antigen binding interactions, the term "pH-dependent binding" means that the antigen-binding activity of the antibody at acidic pH differs from the antigen-binding activity of the antibody at neutral pH.

Various measures of antigen-binding activity may be used as an indicator for the difference in antigen-binding activity at acidic pH versus neutral pH.

In one embodiment, "affinity" of the antibody for its antigen may be used as an indicator of antigen-binding activity. In preferred embodiments, an engineered antibody exhibits "pH-dependent binding" if the affinity of the engineered antibody for its antigen at acidic pH is lower than the affinity of the engineered antibody for its antigen at neutral pH.

In one embodiment, the dissociation rate constant ($k_d$) for the antibody-antigen interaction (also referred to as the antibody off-rate $k_{off}$) may be used as an indicator of antigen-binding activity. In a preferred embodiment, an engineered antibody exhibits "pH-dependent binding" if the dissociation rate constant ($k_d$) for the engineered antibody-antigen interaction at acidic pH is higher than the dissociation rate constant ($k_d$) for the engineered antibody-antigen interaction at neutral pH.

In embodiments wherein the dissociation rate constant ($k_d$) is used as an indicator of pH-dependent binding, the ratio of the dissociation rate constant ($k_d$) for the engineered antibody-antigen interaction at acidic pH to the dissociation rate constant ($k_d$) for the engineered antibody-antigen interaction at neutral pH may be at least 1.5, or at least 2, or at least 5, or at least 10.

In other embodiments, the dissociation rate constant ($k_d$) for the engineered antibody at acidic pH (e.g. pH 5.5) is higher than the dissociation rate constant ($k_d$) for the parental antibody at the same acidic pH. In such embodiments the $k_d$ at acidic pH (e.g. pH 5.5) is increased, as compared to the parental antibody, as a result of the histidine substitutions. In certain embodiments, the ratio of the dissociation rate constant ($k_d$) for the engineered antibody-antigen interaction at acidic pH to the dissociation rate constant ($k_d$) for the parental antibody-antigen interaction at the same acidic pH may be at least 1.5, or at least 2, or at least 5, or at least 10. The dissociation rate ($k_d$) at acidic pH (e.g. pH 5.5) is a particularly relevant measure of pH-dependent binding in view of the antibody recycling pathway in vivo. A faster dissociation of the antibody-antigen complex at acidic pH (pH 5.5-6.0) enables release of the antigen within the acidified endosome.

In one embodiment, the equilibrium dissociation constant ($K_D$) may be used as an indicator of antigen-binding activity. In preferred embodiments, an engineered antibody exhibits "pH-dependent binding" if the equilibrium dissociation constant ($K_D$) for the engineered antibody-antigen interaction at acidic pH is higher than the equilibrium dissociation constant ($K_D$) for the engineered antibody-antigen interaction at neutral pH.

In embodiments wherein the equilibrium dissociation constant ($K_D$) is used as an indicator of pH-dependent binding, the ratio of the equilibrium dissociation constant ($K_D$) for the engineered antibody-antigen interaction at acidic pH to the equilibrium dissociation constant ($K_D$) for the engineered antibody-antigen interaction at neutral pH may be greater than 1.5, or greater than 2, or greater than 5, or greater than 10. In particularly preferred embodiments, the engineered antibody may exhibit 20-40 fold stronger antigen binding at neutral pH versus antigen binding at acidic pH.

In non-limiting embodiments, wherein the equilibrium dissociation constant ($K_D$) is used as an indicator of antigen-binding activity, the engineered antibody may exhibit a equilibrium dissociation constant ($K_D$) for its antigen at acidic pH (e.g. pH 5.5) which is in the range of from 10-20 nM; whereas the $K_D$ of the engineered antibody for its antigen at neutral pH (e.g. pH 7.4) may be around 0.5 nM or less.

Other measures of antigen-binding activity which may be used to indicate pH-dependent binding may include the affinity constant or the association rate constant ($k_a$) or on-rate ($k_{on}$).

For antagonistic antibodies, the measure of antigen-binding activity may be blocking potency, i.e. IC50 in a suitable assay.

In a preferred embodiment, the engineered antibody containing one or more histidine substitutions exhibits greater pH-dependence of binding to its antigen, as compared to the parental antibody. By "greater pH dependence of binding" is meant that the difference between antigen-binding activity at acidic pH and antigen-binding activity at neutral pH is significantly greater for the engineered antibody than for the parental antibody from which it was derived.

In some embodiments, the parental antibody may exhibit no significant pH-dependence of binding to its target antigen, and pH dependence may be introduced into the engineered variant as a consequence of the one or more histidine substitutions. In other embodiments, the parental antibody may exhibit a measurable pH dependence, which is significantly increased in the engineered variant as a consequence of the one or more histidine substitutions.

In certain embodiments, it may be possible to introduce pH-dependence into the engineered antibody without compromising the strength of antigen-antibody binding at neutral pH to a significant extent. In such embodiments, the engineered antibody may exhibit significantly lower antigen-binding activity at acidic pH as compared to the parental antibody from which it was derived, whereas the antigen-binding activity of the engineered antibody at neutral pH may be comparable to that of the parental antibody from which it was derived (i.e. not significantly different).

One advantage of the methods described herein, in which candidate amino acids for histidine substitution are selected according to the "heat map" of natural histidine occurrence in a functional antibody repertoire, is that histidine residues are typically introduced only at "hot spot" amino acid positions where they can occur naturally within the antibody repertoire, and are therefore tolerated within the antibody structure. It has been observed that histidine substitutions at the hot-spot positions may confer pH-dependence of antigen binding, without significantly impacting on the strength of antigen-binding activity at neutral pH.

In one embodiment, the engineered antibody exhibits greater pH-dependence of binding to its antigen, as compared to the parental antibody, whilst retaining at least 80% of the parental antibody's antigen-binding activity at neutral pH. In further embodiments, the engineered antibody may retain at least 80%, at least 85%, at least 90%, at least 95% or 100% of the parental antibody's antigen-binding activity at neutral pH, whilst still exhibiting pH-dependent binding.

In a preferred embodiment, the engineered antibody exhibits greater pH-dependence of binding to its antigen, as compared to the parental antibody, whilst retaining at least 80%, at least 85%, at least 90%, at least 95% or 100% of the parental antibody's affinity for said antigen at neutral pH.

In embodiments wherein the equilibrium dissociation constant ($K_D$) is used as an indicator of antigen-binding activity, the engineered antibody may exhibit an equilibrium dissociation constant ($K_D$) for the target antigen at neutral pH which is no more than 20%, or no more than 15%, or no more than 10%, or no more than 5% greater than the $K_D$ of the parental antibody for the target antigen at neutral pH. In other embodiments, the engineered antibody may exhibit an equilibrium dissociation constant ($K_D$) for the target antigen at neutral pH which is substantially equal to the $K_D$ of the parental antibody for the target antigen at neutral pH.

In other embodiments, the introduction of pH-dependence may result in a reduction in the affinity of the engineered antibody for its antigen at neutral pH. However, depending on the nature of the target antigen, the intended use of the antibody, and also the properties of the parental antibody, a reduction in affinity at neutral pH may be acceptable, provided the desired pH-dependence of binding is achieved. For example, if the parental antibody exhibits particularly high affinity for its antigen at neutral pH, then a reduction in affinity of the engineered antibody for its antigen at neutral pH can be tolerated if this is accompanied by a significant improvement in pH-dependence (i.e. provided that the desired "fold-difference" between binding at neutral pH and binding at acidic pH is achieved). In certain embodiments, the affinity of the engineered antibody for its target antigen at neutral pH may be up to 10-fold, or even 20-fold lower than the affinity of the parental antibody for that antigen at neutral pH, provided that the desired pH-dependence of binding is also achieved.

In each of the foregoing embodiments, "acidic pH" refers to pH in the range of from pH 4.0 to pH 6.5, preferably pH 4.5 to pH 6.0, more preferably pH 5.5 to pH 6.0, and more preferably pH 5.5 to pH 5.8.

In each of the foregoing embodiments "neutral pH" refers to pH in a range of from pH 6.7 to pH 10.0, preferably pH 7.0 to pH 8.0, more preferably pH 7.4.

In particular embodiments, pH-dependent binding may be evaluated by comparing antigen-binding activity of an antibody at acidic pH 5.5 with antigen-binding activity of the same antibody at neutral pH 7.4.

In other embodiments, pH-dependent binding may be evaluated by comparing antigen-binding activity of an antibody at acidic pH6.0 with antigen-binding activity of the same antibody at neutral pH 7.4.

Appropriate methods and conditions for determining antigen-binding activity of an antibody at a defined pH are generally known in the art. By way of example, antigen-binding activity of an antibody at a defined pH can be measured by Biacore® (GE Healthcare), as described in the accompanying experimental examples, by ELISA or using the MSD platform.

Heat-Map of Histidine Occurrence

As described herein, amino acid residues of a parental antibody may be selected for replacement with histidine, or not to be replaced with histidine, based on a "heat-map" of the occurrence of histidine residues at certain amino acid positions within the CDRs of functional antibodies within a natural antibody repertoire. The "heat-map" provides both a list of "hot-spot" amino acid residue positions within the CDRs, and framework positions proximal to the CDRs, at which histidine may occur naturally within the antibody repertoire, and also a list of "cold-spot" amino acid residue positions in the CDRs, and framework positions proximal to the CDRs, at which histidine typically does not naturally occur.

By "antibody repertoire" is meant a population of antibodies displaying antigen-binding activity. A "natural antibody repertoire" is typically a population of antibodies raised by immunisation of a host with target antigen. The repertoire may comprise antibodies against more than one target antigen. In the present disclosure, a "heat-map" of histidine occurrence has been derived from a diverse repertoire of llama antibodies, which was itself derived by immunisation of host animals with multiple different target antigens. The antibodies isolated from these immunizations were also screened by a specific phage display selection, allowing enrichment of antibodies exhibiting pH-dependent antigen binding.

Selection of Residues for Replacement

For any given parental antibody, selection of candidate amino acid residues for replacement with histidine is guided by the heat-map of histidine occurrence.

The terms "substitution" or "replacement" of an amino acid residue are used interchangeably herein. In the context of an engineered antibody which is an engineered variant of a parental antibody, "substitution" requires that an amino acid residue at a defined amino acid position in the parental antibody is replaced with a different amino acid residue, i.e. a histidine residue, which does not naturally occur at that position in the parental antibody.

The "heat-map" of histidine occurrence described herein provides a list of hot-spot amino acid positions at which histidine has been observed to occur naturally. The parental antibody of interest, from which the engineered antibody is to be derived, may naturally contain a histidine residue at one or more of the amino acid positions on the hot-spot list. In these circumstances, the natural histidine residue would generally be retained within the engineered antibody, since it may contribute to pH-dependent antigen binding. However, for the purposes of the methods described herein, this naturally occurring histidine would not be counted as a histidine substitution. The methods described herein therefore require that the engineered antibody must contain at least one additional histidine residue at one or more of the hot-spot amino acid positions, in comparison to the parental antibody from which it was derived. The introduction of one or more additional histidine residues into the engineered antibody may improve pH-dependent binding of the engineered antibody (i.e. lead to greater pH dependence of binding to the target antigen), even for a parental antibody which already includes a hot-spot histidine residue.

Candidate amino acid residues for replacement with histidine are selected from the "hot-spot" list (Table A), in which amino acid positions in the CDRs, and framework positions proximal to the CDRs, of the VH and VL domains are identified according to the KABAT numbering system (Kabat et al., Sequences of Proteins of Immunological Interest, 5th Ed. Public Health Service, National Institutes of Health, Bethesda, MD (1991). The engineered antibody must include at least one histidine substitution at an amino acid position selected from Table A.

Various approaches may be used to select the most appropriate histidine substitutions to confer pH-dependent antigen binding in a parental antibody of interest. If structural information for the binding interaction of the parental antibody to its target antigen is available, then it may be appropriate to employ a "rational design" approach to select candidate amino acids from the hot-spot list for histidine replacement. Hot-spot residues that directly participate in the antigen-antibody binding interaction or that are likely to influence the overall structure of the antigen-binding interface of the parental antibody may be selected based on such structural information. Engineered variants of the parental antibody in which one or more of the selected hot-spot residues, or different combinations thereof, are substituted with histidine may then be synthesised and screened for pH-dependent antigen binding, for example using the screening methods described herein.

Candidate residues for histidine substitution may also be selected based on the variable domain family or subtype of the parental antibody. Described herein are various subtype-specific lists of hot-spot residues, also derived from the heat map of histidine occurrence within the antibody repertoire. In certain embodiments, wherein the variable domain family or subtype of the VH and/or VL domain of the parental antibody is known, candidate residues for histidine substitution may be selected from the following subtype-specific or family-specific hot-spot lists. These lists are not intended to be limiting, but merely provide guidance for the amino acid positions which may be most appropriate for histidine replacement for a particular variable domain family or subtype. For any given variable domain, amino acid positions for possible replacement with histidine may be selected from the complete hot-spot list (Table A), irrespective of the variable domain family or subtype.

For heavy chain variable domains of the VH3 family:

TABLE VH3A (VH3 family hot-spot residues)

| | |
|---|---|
| CDR1 | H31, H32, H33, H35 |
| CDR2 | H50, H52, H52a, H53, H56, H58, H59, H62 |
| CDR3 | H95, H96, H97, H98, H99, H100, H100a, H100b, H100c, H100d, H100e, H100f, H100j, H101, H102 |

TABLE VH3B (VH3 family cold-spot residues)

| | |
|---|---|
| CDR1 | H34, H35a, H35b, H35c |
| CDR2 | H51, H52b, H52c, H54, H55, H57, H60, H61, H63, H64, H65 |
| CDR3 | H100g, H100h, H100i, H100k, H100l, H100m, H100n |

For heavy chain variable domains of the VH1 family:

TABLE VH1A (VH1 family hot-spot residues)

| | |
|---|---|
| CDR1 | H35 |
| CDR2 | H52 |
| CDR3 | H100h, H102 |

TABLE VH1B (VH1 family cold-spot residues)

| | |
|---|---|
| CDR1 | H31, H32, H33, H34, H35a, H35b, H35c |
| CDR2 | H50, H51, H52a, H52b, H52c, H53, H54, H55, H56, H57, H58, H59, H60, H61, H62, H63, H64, H65 |
| CDR3 | H95, H96, H97, H98, H99, H100, H100a, H100b, H100c, H100d, H100e, H100f, H100g, H100i, H100j, H100k, H100l, H100m, H100n, H101 |

For heavy chain variable domains of the VH4 family:

TABLE VH4A (VH4 family hot-spot residues)

| | |
|---|---|
| CDR1 | |
| CDR2 | H50, H52, H63 |
| CDR3 | H95, H100f, H100i, H100l |

TABLE VH4B (VH4 family cold-spot residues)

| | |
|---|---|
| CDR1 | H31, H32, H33, H34, H35, H35a, H35b, H35c |
| CDR2 | H51, H52a, H52b, H52c, H53, H54, H55, H56, H57, H58, H59, H60, H61, H62, H64, H65 |
| CDR3 | H95, H96, H97, H98, H99, H100, H100a, H100b, H100c, H100d, H100e, H100g, H100h, H100j, H100k, H100m, H100n, H101, H102 |

For light chain variable domains of the lambda type:

TABLE VλA (Vλ hot-spot residues)

| | |
|---|---|
| CDR1 | L30, L31, L32, L34, |
| CDR2 | L51, L52, L53, L55, |
| CDR3 | L89, L91, L92, L93, L95a, L95b, L95c, L96 |

TABLE VλB (Vλ cold-spot residues)

| | |
|---|---|
| CDR1 | L24, L25, L26, L27, L27a, L27b, L27c, L27d, L27e, L28, L29, L33 |
| CDR2 | L50, L51a, L51b, L51c, L51d, L54, L56 |
| CDR3 | L90, L94, L95, L95d, L95e, L95f, L97 |

For light chain variable domains of the Vλ1 family:

TABLE Vλ1A

| (Vλ1 family hot-spot residues) | |
| --- | --- |
| CDR1 | L31, L32 |
| CDR2 | |
| CDR3 | L91, L93, L95a, L95b, L96 |

TABLE Vλ1B

| (Vλ1 family cold-spot residues) | |
| --- | --- |
| CDR1 | L24, L25, L26, L27, L27a, L27b, L27c, L27d, L27e, L28, L29, L30, L33, L34 |
| CDR2 | L50, L51, L51a, L51b, L51c, L51d, L52, L53, L54, L55, L56 |
| CDR3 | L89, L90, L92, L94, L95, L95c, L95d, L95e, L95f, L97 |

For light chain variable domains of the Vλ2 family:

TABLE Vλ2A

| (Vλ2 family hot-spot residues) | |
| --- | --- |
| CDR1 | |
| CDR2 | |
| CDR3 | L95a, L96 |
| FR | L87 |

TABLE Vλ2B

| (Vλ2 family cold-spot residues) | |
| --- | --- |
| CDR1 | L24, L25, L26, L27, L27a, L27b, L27c, L27d, L27e, L28, L29, L30, L31, L32, L33, L34 |
| CDR2 | L50, L51, L51a, L51b, L51c, L51d, L52, L53, L54, L55, L56 |
| CDR3 | L89, L90, L91, L92, L93, L94, L95, L95b, L95c, L95d, L95e, L95f, L97 |

For light chain variable domains of the Vλ3 family:

TABLE Vλ3A

| (Vλ3 family hot-spot residues) | |
| --- | --- |
| CDR1 | L31, L32, L34 |
| CDR2 | L51, L52 |
| CDR3 | L89, L91 |
| FR | L49, L87 |

TABLE Vλ3B

| (Vλ3 family cold-spot residues) | |
| --- | --- |
| CDR1 | L24, L25, L26, L27, L27a, L27b, L27c, L27d, L27e, L28, L29, L30, L33 |
| CDR2 | L50, L51a, L51b, L51c, L51d, L53, L54, L55, L56 |
| CDR3 | L90, L92, L93, L94, L95, L95a, L95b, L95c, L95d, L95e, L95f, L96, L97 |

For light chain variable domains of the Vλ5 family:

TABLE Vλ5A

| (Vλ5 family hot-spot residues) | |
| --- | --- |
| CDR1 | L30, L31, L32 |
| CDR2 | L53 |

TABLE Vλ5A-continued

| (Vλ5 family hot-spot residues) | |
| --- | --- |
| CDR3 | L92, L95c, L96 |
| FR | L49, L87 |

TABLE Vλ5B

| (Vλ5 family cold-spot residues) | |
| --- | --- |
| CDR1 | L24, L25, L26, L27, L27a, L27b, L27c, L27d, L27e, L28, L29, L33, L34 |
| CDR2 | L50, L51, L51a, L51b, L51c, L51d, L52, L54, L55, L56 |
| CDR3 | L89, L90, L91, L93, L94, L95, L95a, L95b, L95d, L95e, L95f, L97 |

For light chain variable domains of the Vλ8 family:

TABLE Vλ8A

| (Vλ8 family hot-spot residues) | |
| --- | --- |
| CDR1 | L31 |
| CDR2 | L55 |
| CDR3 | L89, L91, L95b |

TABLE Vλ8B

| (Vλ8 family cold-spot residues) | |
| --- | --- |
| CDR1 | L24, L25, L26, L27, L27a, L27b, L27c, L27d, L27e, L28, L29, L30, L32, L33, L34 |
| CDR2 | L50, L51, L51a, L51b, L51c, L51d, L52, L53, L54, L56 |
| CDR3 | L90, L92, L93, L94, L95, L95a, L95c, L95d, L95e, L95f, L96, L97 |

For light chain variable domains of the kappa type:

TABLE VKA

| (VK hot-spot residues) | |
| --- | --- |
| CDR1 | L27, L27d, L29, L31, L32 |
| CDR2 | L53, L54, L55 |
| CDR3 | L89, L90, L91, L92, L93, L94, L96 |

TABLE VKB

| (VK cold-spot residues) | |
| --- | --- |
| CDR1 | L24, L25, L26, L27A, L27b, L27c, L27e, I27f, L28, L30, L33, L34 |
| CDR2 | L50, L51, L51a, L51b, L51c, L51d, L52, L56 |
| CDR3 | L95, L95a, L95b, L95c, L95d, L95e, L95f, L97 |

For light chain variable domains of the VK1 family:

TABLE VK1A

| (VK1 family hot-spot residues) | |
| --- | --- |
| CDR1 | L31, L32 |
| CDR2 | |
| CDR3 | L89, L90, L91, L93 |

TABLE VK1B (VK1 family cold-spot residues)

| | |
|---|---|
| CDR1 | L24, L25, L26, L27, L27a, L27b, L27c, L27d, L27e, L28, L29, L30, L33, L34 |
| CDR2 | L50, L51, L51a, L51b, L51c, L51d, L52, L53, L54, L55, L56 |
| CDR3 | L92, L94, L95, L95a, L95b, L95c, L95d, L95e, L95f, L96, L97 |

For light chain variable domains of the VK2 family:

TABLE VK2A (VK2 family hot-spot residues)

| | |
|---|---|
| CDR1 | L27, L27d, L32 |
| CDR2 | L53, L54, L55 |
| CDR3 | L91, L93, L94, L96 |

TABLE VK2B (VK2 family cold-spot residues)

| | |
|---|---|
| CDR1 | L24, L25, L26, L27a, L27b, L27c, L27e, L28, L29, L30, L31, L33, L34 |
| CDR2 | L50, L51, L51a, L51b, L51c, L51d, L52, L56 |
| CDR3 | L89, L90, L92, L95, L95a, L95b, L95c, L95d, L95e, L95f, L97 |

For light chain variable domains of the VK4 family:

TABLE VK4A (VK4 family hot-spot residues)

| | |
|---|---|
| CDR1 | L27, L29 |
| CDR2 | L54 |
| CDR3 | L90, L91, L92 |

TABLE VK4B (VK4 family cold-spot residues)

| | |
|---|---|
| CDR1 | L24, L25, L26, L27a, L27b, L27c, L27d, L27e, L28, L30, L31, L32, L33, L34 |
| CDR2 | L50, L51, L51a, L51b, L51c, L51d, L52, L53, L55, L56 |
| CDR3 | L89, L93, L94, L95, L95a, L95b, L95c, L95d, L95e, L95f, L96, L97 |

Screening of Panels of Variants

Particular embodiments of the methods of the invention may be based on construction of a panel of engineered variants of a parental antibody which is then screened in order to identify one or more engineered variants exhibiting the desired pH-dependent binding. Construction of the panel of variants allows systematic mutational analysis of a large number of possible histidine replacements at amino acid positions defined by the heat map. This method differs from prior art combinatorial methods in that the construction of the panel of variants is guided by the heat-map of histidine occurrence, hence it is not necessary or desirable to sample all possible amino acid positions in the CDRs, and combinations thereof, as candidates for histidine replacement.

The systematic mutational analysis methods described herein generally comprise the steps of:
(a) providing a parental antibody which binds to an antigen;
(b) preparing a panel of engineered variants of said parental antibody, wherein each of said engineered variants in said panel differs from said parental antibody by substitution of at least one amino acid residue with a histidine residue, wherein at least one amino acid residue selected from the hot-spot list (Table A) is substituted with histidine and at least one amino acid residue selected from the cold-spot list (Table B) is not substituted with histidine;
(c) screening said panel of engineered variants for pH dependent binding to said antigen and thereby identifying an engineered antibody exhibiting pH-dependent binding to said antigen.

This method requires the preparation of a panel of engineered variants of the parental antibody of interest, wherein each of the engineered variants in the panel differs from the parental antibody by substitution of at least one amino acid with histidine. Selection of amino acid positions for replacement with histidine is also based on the heat-map of histidine occurrence. Each of the engineered variants in the panel must contain at least one histidine substitution at an amino acid position selected from the hot-spot list (Table A), whereas at least one amino acid residue selected from the cold-spot list (Table B) is not substituted with histidine. Preferably, each of the engineered variants in the panel will comprise a different pattern of histidine substitution, so as to allow the effects of different histidine substitutions on pH-dependent antigen binding to be analysed in parallel.

In one embodiment of the method, each of the engineered variants in the panel may comprise a single histidine substitution at one of the hot-spot amino acid positions listed (Table A). Preferably each of the engineered variants in the panel comprises a different histidine substitution at one of the hot-spot amino acid positions listed (Table A). Such a panel allows the effect of histidine substitution at individual hot-spot amino acid positions on pH-dependent binding to be analysed. The panel of engineered variants may be representative of the entire hot-spot list, i.e. may include variants having single histidine substitutions at each of the amino acid positions listed in Table A, or may be representative of a selected sub-set of the hot-spot list, such as for example a sub-set of substitutions relevant to one or more specific variable domain families or subtypes. In addition, the panel may also include variants comprising histidine substitutions at one or more of the "cold-spot" positions within VH CDR3 or VL CDR3.

In other embodiments, the panel prepared in step (b) may include engineered variants comprising different combinations of two or more, three of more, four or more or five or more histidine substitutions, with the proviso that at least one of said substitutions must be at a hot-spot amino acid position selected from Table A, whereas at least one amino acid from Table B is not substituted with histidine. Preferably, all of said histidine substitutions are made at hot-spot amino acid positions selected from Table A. This panel allows screening for combinations of histidine substitutions (and in particular combinations of hot-spot histidine substitutions) that confer pH-dependent binding. In addition, the panel may also include variants comprising histidine substitutions at one or more of the "cold-spot" positions within VH CDR3 or VL CDR3, optionally in combination with histidine substitutions at one or more of the hot-spot amino acid positions.

In certain embodiments, an initial screen may be performed on a panel of engineered variants containing single histidine substitutions, as described above, in order to identify single amino acid positions at which histidine substitution can confer pH-dependent binding. Based on the results of this initial screen, one or more further engineered variants may be constructed in which histidine substitutions previously identified as conferring pH-dependent binding are combined. Such a method may comprise the following steps:
- (a) identifying a parental antibody which binds to an antigen;
- (b) preparing a panel of engineered variants of said parental antibody, wherein each of said engineered variants in said panel differs from said parental antibody by substitution of at least one amino acid residue with a histidine residue, wherein at least one amino acid residue selected from the hot-spot list (Table A) is substituted with histidine and at least one amino acid residue selected from the cold-spot list (Table B) is not substituted with histidine, (preferably wherein each of said engineered variants comprises a different pattern of histidine substitution);
- (c) screening said panel of engineered variants for pH dependent binding to said target antigen and thereby identifying selected amino acid positions at which the presence of histidine confers pH dependent binding to said antigen;
- (d) preparing one or more further engineered variants of said parental antibody, wherein each of said variants comprises histidine at two or more selected amino acid positions identified in step (c); and
- (e) screening said further engineered variants for pH dependent binding to said antigen; and thereby identifying an engineered antibody exhibiting pH dependent binding to said antigen.

In particular embodiments of the method, histidine substitutions in the VH domain and the VL domain may be analysed separately for their effects on pH-dependent binding. Accordingly, in one embodiment step (b) comprises preparing a panel of engineered variants of said parental antibody, wherein each of said engineered variants in said panel differs from said parental antibody by substitution of at least one amino acid residue in the VH domain with a histidine residue, wherein at least one amino acid residue selected from the heavy chain hot-spot list (Table HA) is substituted with histidine and at least one amino acid residue selected from the heavy chain cold-spot list (Table HB) is not substituted with histidine. In addition, the panel may also include variants comprising histidine substitutions at the "cold-spot" positions within VH CDR3.

Typically, the engineered variants will comprise a mutant VH domain, comprising one or more histidine substitutions, paired with the VL domain of the parental antibody. Such libraries allow screening for histidine substitutions in the VH domain which confer pH-dependent binding.

TABLE HA (VH hot-spot residue positions)

| | |
|---|---|
| VH CDR1 | H31, H32, H33, H35, |
| VH CDR2 | H50, H52, H52a, H53, H56, H58, H59, H62, H63, |
| VH CDR3 | H95, H96, H97, H98, H99, H100, H100a, H100b, H100c, H100d, H100e, H100f, H100h, H100i, H100j, H100l, H101, H102 |

TABLE HB (VH cold-spot residue positions)

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |

In a further embodiment, step (b) comprises preparing a panel of engineered variants of said parental antibody, wherein each of said engineered variants in said panel differs from said parental antibody by substitution of at least one amino acid residue in the VL domain with a histidine residue, wherein at least amino acid residue selected from the light chain hot-spot list (Table LA) is substituted with histidine and at least one amino acid residue selected from the light chain hot-spot list (Table LB) is not substituted with histidine. In addition, the panel may also include variants comprising histidine substitutions at the "cold-spot" positions within VL CDR3.

Typically, the engineered variants will comprise a mutant VL domain, comprising one or more histidine substitutions, paired with the VH domain of the parental antibody. Such libraries allow screening for histidine substitutions in the VL domain which confer pH-dependent binding.

TABLE LA (VL hot-spot residue positions)

| | |
|---|---|
| VL CDR1 | L27, L27d, L29, L30, L31, L32, L34 |
| VL CDR2 | L51, L52, L53, L54, L55 |
| VL CDR3 | L89, L90, L91, L92, L93, L94, L95, L95a, L95b, L95c, L95d, L95e, L95f, L96, L97 |

TABLE LB (VL cold-spot residue positions)

| | |
|---|---|
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 |

For light chain variants of the lambda class, the "hot spot" and "cold spot" residue positions may be selected from the following lists:

TABLE VλA (Vλ hot-spot residues)

| | |
|---|---|
| CDR1 | L30, L31, L32, L34, |
| CDR2 | L51, L52, L53, L55, |
| CDR3 | L89, L91, L92, L93, L95a, L95b, L95c, L96 |

TABLE VλB (Vλ cold-spot residues)

| | |
|---|---|
| CDR1 | L24, L25, L26, L27, L27a, L27b, L27c, L27d, L27e, L28, L29, L33 |
| CDR2 | L50, L51a, L51b, L51c, L51d, L54, L56 |
| CDR3 | L90, L94, L95, L95d, L95e, L95f, L97 |

For light chain variants of the kappa class, the "hot spot" and "cold spot" residue positions may be selected from the following lists:

TABLE VKA (VK hot-spot residues)

| | |
|---|---|
| CDR1 | L27, L27d, L29, L31, L32 |
| CDR2 | L53, L54, L55 |
| CDR3 | L89, L90, L91, L92, L93, L94, L96 |

TABLE VKB (VK cold-spot residues)

| | |
|---|---|
| CDR1 | L24, L25, L26, L27A, L27b, L27c, L27e, I27f, L28, L30, L33, L34 |
| CDR2 | L50, L51, L51a, L51b, L51c, L51d, L52, L56 |
| CDR3 | L95, L95a, L95b, L95c, L95d, L95e, L95f, L97 |

In certain embodiments, VH and VL domain histidine substitutions identified by means of separate initial VH and VL domain screens may be combined in a single engineered variant. A further screen may then be performed to identify VH and VL combinations exhibiting pH-dependent binding. Such a method may comprise the following steps:

(a) identifying a parental antibody which binds to an antigen;

(b) preparing a first panel of engineered variants of said parental antibody, wherein each of said engineered variants in said panel differs from said parental antibody by substitution of at least one amino acid residue in the VH domain with a histidine residue, wherein at least one amino acid residue selected from the heavy chain hot-spot list (Table HA) is substituted with histidine and at least one amino acid residue selected from the heavy chain cold-spot list (Table HB) is not substituted with histidine;

(c) screening said first panel of engineered variants for pH dependent binding to said antigen; and thereby identifying one or more selected amino acid positions in the VH domain at which the presence of histidine confers pH dependent binding;

(d) preparing a second panel of engineered variants of said parental antibody, wherein each of said engineered variants in said panel differs from said parental antibody by substitution of at least one amino acid residue in the VL domain with a histidine residue, wherein at least one amino acid residue selected from the light chain hot-spot list (Table LA) is substituted with histidine and at least one amino acid residue selected from the light chain hot-spot list (Table LB) is not substituted with histidine;

(e) screening said second panel of engineered variants for pH dependent binding to said antigen; and thereby identifying one or more selected amino acid positions in the VL domain at which the presence of histidine confers pH dependent binding;

(f) preparing one or more further engineered variants of said parental antibody, wherein each of said variants differs from said parental antibody by substitution of the amino acid at one or more of the selected amino acid positions in the VH domain identified in step (c) with histidine and by substitution of the amino acid at one or more of the selected amino acid positions in the VL domain identified in step (e) with histidine; and (g) screening said further engineered variants for pH dependent binding to said antigen; and thereby identifying an engineered antibody exhibiting pH-dependent binding to said antigen.

This approach enables the identification of synergies between histidine mutations identified in the initial (separate) VH and VL domain screens. For example, the best performing VH mutations (i.e. those conferring the greatest degree of pH dependence) may be combined with a number of different VL mutations, or the best performing VL mutations combined with different VH mutations, in order to identify synergistic effects between different combinations of VH and VL domain mutations. In this embodiment it is permissible to also include histidine substitutions at the "cold-spot" positions within VH CDR3 or VL CDR3, and combinations thereof.

Screening Methods

Various screening methods may be used to identify engineered antibodies exhibiting pH-dependent binding to a target antigen. Such screening methods may comprise steps of:

(a) determining the antigen-binding activity of the engineered antibody at acidic pH;

(b) determining the antigen-binding activity of the engineered antibody at neutral pH;

(c) selecting an engineered antibody whose antigen-binding activity at acidic pH differs from that at neutral pH.

Appropriate methods and conditions for determining antigen-binding activity at a defined pH are generally known in the art. By way of example, antigen-binding activity of an antibody at a defined pH can be determined by Biacore® (GE Healthcare), as described in the accompanying experimental examples. Other suitable techniques include ELISA or MSD, which may be used to determine antigen binding at a specific antibody concentration (such as EC50), under different pH conditions (e.g. pH 7.4 and pH 5.5).

The methods described herein may include steps of measuring the antigen binding activity of the engineered antibody at neutral pH and at acidic pH, and comparing one or more parameters of the binding at neutral pH and/or acidic pH in order to determine that the engineered antibody exhibits pH-dependent binding.

In certain embodiments the antigen-binding activity of the engineered antibody may be measured by dual pH ELISA, as described in the accompanying examples. In this set-up, initial binding of the antibody to antigen is assessed at neutral pH (e.g. pH 7.4), followed by a washing step at acidic pH (e.g. pH 5.5). This allows discrimination between the effects of pH on antibody association, dissociation or both, and may be more representative of the in vivo situation where antibody binding to target antigen occurs at neutral pH, and release of the antigen takes place at acidic endosomal pH.

Typically, the selected engineered antibody will exhibit lower affinity for its antigen at acidic pH than at neutral pH. In an initial screen, any significant difference in affinity at acidic pH versus affinity at neutral pH may be indicative of pH-dependent binding.

The dissociation rate constant ($k_d$), i.e. the off-rate, for the engineered antibody-antigen interaction at acidic pH may be higher than the dissociation rate constant ($k_d$) for the engineered antibody-antigen interaction at neutral pH. In an initial screen, any significant difference in ($k_d$) at acidic pH versus ($k_d$) at neutral pH may be indicative of pH-dependent binding. In other embodiments the ratio of the dissociation rate constant ($k_d$) for the engineered antibody-antigen interaction at acidic pH to the dissociation rate constant ($k_d$) for the engineered antibody-antigen interaction at neutral pH may be at least 1.5, or at least 2, or at least 5, or at least 10. When multiple histidine mutations are combined, the overall degree of pH-dependence may be increased.

The equilibrium dissociation constant ($K_D$) for the engineered antibody-antigen interaction at acidic pH may be higher than the equilibrium dissociation constant ($K_D$) for the engineered antibody-antigen interaction at neutral pH. In an initial screen, any significant difference in $K_D$ at acidic pH versus $K_D$ at neutral pH may be indicative of pH-dependent binding. The ratio of the equilibrium dissociation constant ($K_D$) for the engineered antibody-antigen interaction at acidic pH to the equilibrium dissociation constant ($K_D$) for the engineered antibody-antigen interaction at neutral pH may be greater than 1.5, or greater 2, or greater than 5, or greater than 10.

When multiple histidine mutations are combined, the overall degree of pH-dependence may be increased. In particularly preferred embodiments, combining histidine mutations may achieve around 20-40 fold stronger antigen binding at neutral pH versus antigen binding at acidic pH.

As explained elsewhere herein, improvements in pH-dependent binding may be achieved with or without significant impact on affinity for the target antigen at neutral pH.

In non-limiting embodiments, wherein the equilibrium dissociation constant ($K_D$) is used as an indicator of antigen-binding activity, the engineered antibody may exhibit an equilibrium dissociation constant ($K_D$) for its antigen at acidic pH (e.g. pH 5.5) which is in the range of from 10-20 nM; whereas the $K_D$ of the engineered antibody for its antigen at neutral pH (e.g. 7.4) may be around 0.5 nM or less.

In each of the foregoing embodiments, "acidic pH" refers to pH in the range of from pH 4.0 to pH 6.5, preferably pH 4.5 to pH 6.0, more preferably pH 5.5 to pH 6.0, and more preferably pH 5.5 to pH 5.8.

In each of the foregoing embodiments "neutral pH" refers to pH in a range of from pH 6.7 to pH 10.0, preferably pH 7.0 to pH 8.0, more preferably pH 7.4.

In particular embodiments, pH-dependent binding may be evaluated by comparing antigen-binding activity of an antibody at acidic pH 5.5 with antigen-binding activity of the same antibody at neutral pH 7.4.

In other embodiments, pH-dependent binding may be evaluated by comparing antigen-binding activity of an antibody at acidic pH 6.0 with antigen-binding activity of the same antibody at neutral pH 7.4.

The methods described herein may, additionally or alternatively, include steps of measuring the antigen-binding activity of the parental antibody at acidic pH and/or at neutral pH and comparing parameters of this binding interaction to the corresponding binding parameters of the engineered antibody-antigen interaction.

The dissociation rate constant ($k_d$) for the engineered antibody at acidic pH (e.g. pH 5.5) may be higher than the dissociation rate constant ($k_d$) for the parental antibody at the same acidic pH. In such embodiments the $k_d$ at acidic pH (e.g. pH 5.5) is increased, as compared to the parental antibody, as a result of the histidine substitutions. The ratio of the dissociation rate constant ($k_d$) for the engineered antibody-antigen interaction at acidic pH to the dissociation rate constant ($k_d$) for the parental antibody-antigen interaction at the same acidic pH may be at least 1.5, or at least 2, or at least 5, or at least 10.

Engineered Antibodies

Also provided herein is an engineered antibody exhibiting pH dependent binding to its antigen wherein at least one amino acid in the CDRs of the engineered antibody is a histidine residue, characterised in that at least one amino acid residue selected from the hot-spot list (Table A) is a histidine residue and at least one amino acid residue from the cold-spot list (Table B) is not a histidine residue.

By "engineered antibody" is meant an antibody whose amino acid sequence has been deliberately altered or mutated in vitro. In the present disclosure, "engineered antibodies" are antibody variants in which the amino acid sequences of the CDRs of the antibody have been deliberately altered or mutated in order to introduce one or more additional histidine residues.

The CDRs of antibody VL and VH domains can typically be defined as comprising the following amino acids: residues 24-34 (CDRL1), 50-56 (CDRL2) and 89-97 (CDRL3) in the light chain variable domain, and residues 31-35 or 31-35c (CDRH1), 50-65 (CDRH2) and 95-102 (CDRH3) in the heavy chain variable domain (Kabat et al., Sequences of Proteins of Immunological Interest, 5th Ed. Public Health Service, National Institutes of Health, Bethesda, MD (1991)).

The engineered antibody may include a total of 1, 2, 3, 4, 5, or more histidine residues in the CDRs of the VH domain, or the VL domain or both the VH domain and the VL domain.

At least one of the histidine residues in the CDRs of the engineered antibody must occur at an amino acid position selected from the "hot-spot" list (Table A). In certain embodiments at least two, at least three, at least four, or at least five of the histidine residues must occur at amino acid positions selected from the "hot spot" list. In certain embodiments, all of the histidine residues in the engineered antibody occur at amino acid positions selected from the hot-spot list (Table A), As described herein, there are certain amino acid positions in the CDRs of the engineered antibody that are preferably not occupied by histidine residues. These amino acid positions are those shown on the "cold-spot" list (Table B). The engineered antibodies must include at least one amino acid position on the cold-spot list (Table B) which is not occupied by a histidine residue. In certain embodiments, at least two, at least three, at least four, or at least five of the amino acid positions on the cold-spot list (Table B) are not histidine. In further embodiments, none of the amino acid positions on the cold-spot list (Table B) are histidine. As an exception to this, in certain embodiments it is permissible to also include histidine substitutions at the "cold-spot" positions within VH CDR3 or VL CDR3, and combinations thereof.

The engineered antibody exhibits pH-dependent binding to its antigen, meaning that the antigen-binding activity of the antibody at acidic pH differs from the antigen-binding activity of the antibody at neutral pH.

In one embodiment, the engineered antibody has lower affinity for its antigen at acidic pH than at neutral pH.

In one embodiment, the dissociation rate constant ($k_d$) for the engineered antibody-antigen interaction at acidic pH is higher than the dissociation rate constant ($k_d$) for the engineered antibody-antigen interaction at neutral pH.

In one embodiment, the equilibrium dissociation constant ($K_D$) for the engineered antibody-antigen interaction at acidic pH is higher than the equilibrium dissociation constant ($K_D$) for the engineered antibody-antigen interaction at neutral pH.

In particularly preferred embodiments, the engineered antibody may exhibit 20-40 fold stronger antigen binding at neutral pH versus antigen binding at acidic pH.

In non-limiting embodiments, wherein the equilibrium dissociation constant ($K_D$) is used as an indicator of antigen-binding activity, the engineered antibody may exhibit an equilibrium dissociation constant ($K_D$) for its antigen at acidic pH (e.g. pH 5.5) which is in the range of from 10-20 nM; whereas the $K_D$ of the engineered antibody for its antigen at neutral pH (e.g. 7.4) may be around 0.5 nM or less.

Structure of the Engineered Antibody

The engineered antibodies described herein are typically four-chain immunoglobulins of the conventional type, in which antigen-binding specificity is provided by paired VH and VL domains, contributing six CDRs to the antigen-binding site. However, the term "engineered antibodies" also encompasses antigen-binding fragments of conventional immunoglobulins and engineered antigen-binding constructs, including but not limited to Fab, F(ab'), F(ab')$_2$, Fv, scFv, diabodies, triabodies, minibodies etc, and any other modified immunoglobulin configuration comprising an antigen binding site provided by paired VH and VL domains.

The engineered antibodies may comprise a constant region, comprising one or more or all of a CH1 domain, hinge region, CH2 domain and CH3 domain. In particular, the engineered antibodies may comprise an Fc region (comprised of CH2 and CH3 domain) which may confer one or more antibody effector functions. The Fc region of the engineered antibody may itself by engineered or modified in order to confer useful functional properties.

The engineered antibody may be of any antibody class including: IgA, IgD, IgE, IgG, or IgM. In preferred embodiments, the engineered antibody is an IgG. The engineered antibody may be an IgG of any subclass (isotype) including: IgG1, IgG2, IgG3 or IgG4.

In a preferred embodiment, the engineered antibody may comprise an Fc region that is capable of binding to the neonatal Fc receptor (FcRn). In particular, it may be desirable for the Fc region to exhibit strong binding affinity for FcRn at neutral pH. The Fc region of the engineered antibody may be modified in order to enhance binding to the neonatal Fc receptor, FcRn. Examples of Fc modifications conferring increased binding to FcRn include amino acid substitutions at one or more amino acid positions in the CH2 and/or CH3 domains of the Fc region.

Suitable Fc mutations include the Abdeg™ mutations described by Vaccaro et al., Nature Biotechnology, Vol. 23, 1283-1288 (2005). Abdeg™ mutants are engineered variants of human IgG, including but not limited to human IgG1, containing mutations of Met252, Ser254, Thr256, His 433 and Asn434 to Tyr252, Thr254, Glu256, Lys433 and Phe434 (EU numbering). Engineered antibodies (e.g. engineered human IgG1) carrying the Abdeg™ mutations exhibit enhanced affinity for binding to FcRn relative to their wild type counterparts, and bind more stably to FcRn during exocytic events at the cell surface. Preferred engineered antibodies combine one or more histidine substitutions in the CDRs of the variable domains, as defined herein, with Abdeg mutations in the Fc region.

Further suitable Fc mutations include the NHance™ mutations described in U.S. Pat. No. 8,163,881. NHance™ mutants are engineered variants of human IgG, including but not limited to human IgG1, containing mutations of His 433 and Asn434 to Lys433 and Phe434 (EU numbering). Engineered antibodies (e.g. engineered human IgG1) carrying the NHance™ mutations exhibit enhanced affinity for binding to FcRn relative to their wild type counterparts. Preferred engineered antibodies combine one or more histidine substitutions in the CDRs of the variable domains, as defined herein, with NHance™ mutations in the Fc region.

In a preferred embodiment, the engineered antibody may comprise variable domains (VH and VL) that are engineered variants of the variable domains of a camelid-derived antibody (e.g. a llama antibody) comprising one or more histidine substitutions in the CDRs, and the Fc region of a human IgG (e.g. human IgG1) comprising the Abdeg™ mutations Tyr252, Thr254, Glu256, Lys433 and Phe434 (EU numbering)

In a further preferred embodiment, the engineered antibody may comprise variable domains (VH and VL) that are engineered variants of the variable domains of a camelid-derived antibody (e.g. a llama antibody) comprising one or more histidine substitutions in the CDRs, and the Fc region of a human IgG (e.g. human IgG1) comprising the NHance™ mutations Lys433 and Phe434 (EU numbering).

Engineered antibodies exhibiting the dual properties of pH-dependent antigen binding, plus increased binding affinity for FcRn, can exert an active antigen removal effect, and are useful for eliminating soluble antigens from plasma in vivo. The concept of "active antigen removal" utilises engineered antibodies to mimic the action of cell-surface endocytic receptors, enabling selective elimination of the target antigen from plasma. In brief, engineered antibodies bind to the corresponding antigen present in plasma (at neutral pH) to form an antigen-antibody complex. This complex is randomly absorbed into the endosomes (usually via pinocytosis) where the antibody Fc part will bind to the FcRn when the pH becomes acidic. Due to the pH-dependent antigen binding property of the engineered antibody, bound antigen will be released in the acidic endosome and targeted for degradation via a lysosome pathway. The free antibody (still bound to FcRn, but no longer bound to its antigen) will be then be recycled back to the cell surface, where it can participate in further rounds of antigen binding and internalisation. Fc mutations that favour binding to FcRn at acidic pH without substantially affecting the binding at pH 7.4 are able to enhance this "active antigen removal" process.

In addition to the specific Fc mutations listed above, the engineered antibodies may also include any other mutation or modification which improves the uptake of antibodies in the endosomes, including for example changes in pI, changes in charge, changes in FcRn affinity at pH 7.4 and/or pH6.0; any mutation or modification which promotes increased binding to any other "high recycling" Fc receptor such for example the Fcγ receptors, especially FcγRIIb; or any mutation that increase immune complex formation (e.g. complement binding sites).

The engineered antibody may be an engineered variant of a parental antibody from human, murine, rat, rabbit, camelid, or other mammalian species, or a chimeric antibody. In particular embodiments, the engineered antibody may be an engineered variant of a camelid antibody isolated from a camelid species such as llama, camel, dromedary, guanaco, vicuña, etc, or an engineered variant of a camelid-human chimeric antibody (e.g. a llama-human chimera), in which the variable domains (or CDRs thereof) are derived from a camelid species (e.g. llama) and the constant domains are human. Techniques for the production of camelid antibodies, and camelid-human chimeric antibodies are described in WO 2010/001251, the contents of which are incorporated herein by reference.

The antigen-binding specificity of the engineered antibody, i.e. the nature of the target antigen to which it binds, is not particularly limited. The applicant has demonstrated that the methodology provided herein is applicable to the engineering of pH-dependent variants of a number of different parental antibodies with different antigen-binding properties. Hence, the described techniques for engineering of pH-dependent antigen binding represent a principle of general application, which is not limited to antibodies binding one specific target antigen.

Exemplification

The present invention is further illustrated by the following examples, which should not be construed as further limiting. The contents of all references, patents and published patent applications cited throughout this application are expressly incorporated herein by reference.

EXAMPLE 1: CONSTRUCTION OF THE HEAT MAP

In order to identify the amino acid residue positions in the V domains at which histidine residues are naturally allowed within a large antibody repertoire, the sequences of the VH, Vlambda and Vkappa domains of large number of functional (antigen-binding) antibodies, or corresponding Fab fragments, from several target antigen projects were pooled and analysed.

Each target antigen project comprised active llama immunization with purified antigen or DNA expressing the target (DNA vaccination), Fab or scFv phage display library construction and phage display selection and screening for specific binders. The phage display was done according to standard procedure, usually up to 3 rounds of selection using trypsin as eluting agent followed by expression of the Fab (or scFv) in the periplasmic extract and identification of the Fab (or scFv) binders by ELISA, MSD or SPR (Biacore). In addition to the trypsin elution, and to further enrich for antibodies with pH dependent binding, a parallel phage display process was followed where a pH 5.5 elution in TBS (50 mM Tris pH 5.5, and 150 mM NaCl) was used for up to 3 rounds of selections. All the sequences were then pooled, subdivided in type (VH, Vlambda or Vkappa) and subfamily (for ex VH1, VH2 and VH3). Any exact duplicate sequences were removed and only unique sequences were used to count the number of histidine residues at each position of the V domain. This led to the creation of a "Heat map" showing at which amino acid positions an histidine is accepted in the V domains of immunized llama derived antibodies. In addition, this data set can be further complemented using sequences identified by high throughput sequencing using the RNA from immunized llama.

EXAMPLE 2: USE OF THE HEAT MAP TO INCREASE PH DEPENDENCY

A parental antibody, or Fab fragment, with the required characteristics in term of high affinity, functionality (e.g. blocking of the ligand:receptor interaction) and preferably some pH dependency was selected for Histidine engineering using the heat map.

Figure 1:
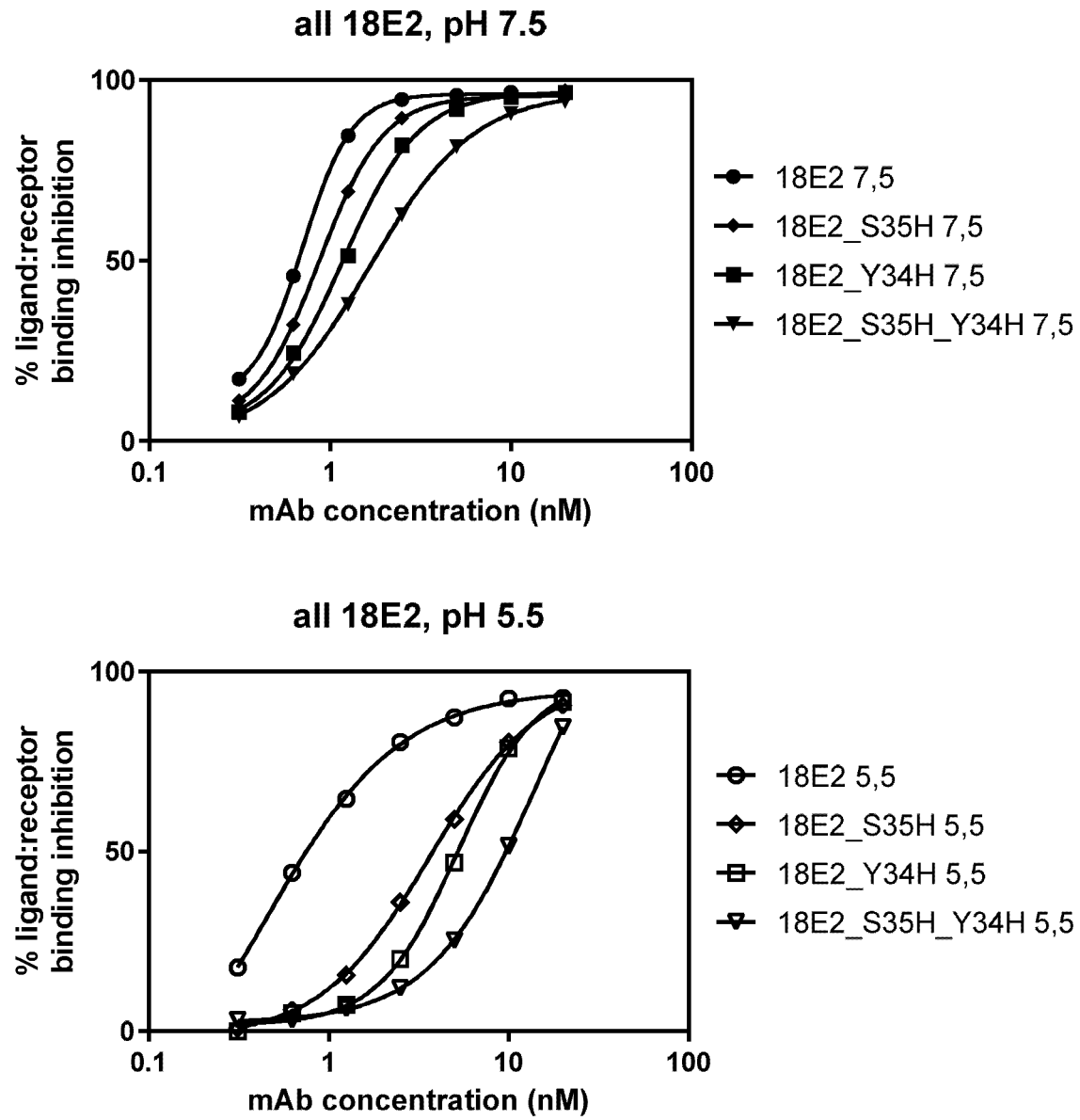
FIG. 1: illustrates pH dependent antigen binding in engineered variants of parental antibody 18E2, as measured using a functional assay. IC50 for inhibition of ligand:receptor interaction was measured for parental antibody 18E2, and engineered variants of 18E2 containing one or two defined histidine mutations, at both pH 7.4 and pH5.5.

Initially a few histidine mutations were tested on a single parental antibody. Antibody 18E2 was mutated in the VH domain at position H35 and in the VL domain at position L34. Because the target antigen of this antibody was not amenable for Biacore® due to the presence of a conformational epitope, the effect of the pH dependency was measured on the capacity of the antibody to block the ligand:receptor interaction. The IC50 was measured when all the proteins are incubated at pH 7.4 or at pH 5.5, and the results are shown in Table 1 and FIG. 1. The data suggest that a 4-fold increase in pH dependency was observed for this antibody when the single mutation was introduced. Interestingly, the combination of the mutated VH with the mutated Vlambda improved further the pH dependency without too much effect at pH 7.4.

TABLE 1

|  | IC50 (μg/ml) | Fold diff. |
|---|---|---|
| 18E2 pH7.4 | 0.7 |  |
| 18E2 pH5.5 | 0.4 | 0.6 (*) |
| 18E2_S35H(VH) pH7.4 | 0.9 |  |
| 18E2_S35H(VH) pH5.5 | 3.6 | 4.2 |
| 18E2_Y34H(VL) pH7.4 | 1.2 |  |
| 18E2_Y34H(VL) pH5.5 | 5.2 | 4.4 |
| 18E2_S35H(VH)_Y34H(VL) pH7.4 | 1.7 |  |
| 18E2_S35H(VH)_Y34H(VL) pH5.5 | 14.5 | 8.8 |

These data confirmed that the replacement of an amino acid by histidine at position defined by the heat map is working, i.e. can enhance pH dependency. Because it can be expected that histidine mutations at other positions may produce a better (or worse) effect, a systematic mutational analysis was done.

EXAMPLE: 3 FULL MUTATION ANALYSIS USING THE HEAT MAP TO INCREASE PH DEPENDENCY

The pH dependency of antibody 5D1 directed against a second antigen target was introduced using the heat map. According to the heat map, 18 positions were amenable for histidine replacement in the VH of 5D1 and 12 in the Vlambda of 5D1 (see table 2). Note that histidine residues were naturally present at positions 55 and 91 of the VL, reducing further the number of mutants to be tested. Because the closest germline of the VL is a VL8, the position L49 in FR2 was not mutated to histidine in the initial screens. However, based on the structural conservation of the CDR2 loop this position could have been mutated as well according to the heat map.

TABLE 2

| VH5D1 | IGHV3-23*01 | VL5D1 | VL8-61*01 |
|---|---|---|---|
| VH5D1m1 | 31 | HCDR1 | VL5D1m1 | 31 | LCDR1 |
| VH5D1m14 | 33 |  | VL5D1m2 | 32 |  |
| VH5D1m2 | 35 |  | VL5D1m3 | 34 |  |
| VH5D1m15 | 50 | HCDR2 | VL5D1m4 | 51 | LCDR2 |
| VH5D1m3 | 52 |  | VL5D1m5 | 52 |  |
| VH5D1m4 | 52a |  | (natural H) | 55 |  |
| VH5D1m16 | 53 |  |  |  |  |
| VH5D1m5 | 56 |  |  |  |  |
| VH5D1m6 | 58 |  | VL5D1m6 | 89 | LCDR3 |
| VH5D1m7 | 62 |  | VL5D1m7 | 90 |  |
| VH5D1m8 | 95 | HCDR3 | (natural H) | 91 |  |
| VH5D1m9 | 96 |  | VL5D1m8 | 92 |  |
| VH5D1m10 | 97 |  | VL5D1m9 | 93 |  |
| VH5D1m11 | 98 |  | VL5D1m10 | 94 |  |

TABLE 2-continued

| VH5D1 | IGHV3-23*01 | VL5D1 | VL8-61*01 |
|---|---|---|---|
| VH5D1m12 | 99 | VL5D1m11 | 96 |
| VH5D1m13 | 100 | VL5D1m12 | 97 |
| VH5D1m17 | 101 | | |
| VH5D1m18 | 102 | | |

For each mutation, a synthetic gene was ordered (Geneart, Thermo Scientific). The lyophilized DNA was diluted in H$_2$O and recloned in a mammalian expression vector containing the human constant domains (CH1-CH2-CH3 for the VH or Clambda for the VLambda or Ckappa for the Vkappa) using standard DNA recloning method (restriction enzyme and T4 ligase). The generated constructs were sequence verified and used to transiently transfect 10 ml of HEK293 cells in suspension to produce a panel of engineered variant antibodies, each containing a single HIS substitution.

Each single VH 5D1 mutant was transfected individually with the wild-type light chain, whilst each single VL 5D1 mutant was transfected individually with the wild-type heavy chain. HEK293 cells were grown in Freestyle 293 Expression Medium (Gibco) at 37° C., 5% CO$_2$ and transfections were performed at an optimal density of 0.5-0.8× 10$^6$ cells/mL. The transfection mixture contained 40 µL of OPTI-MEM (Gibco), 1.5 µg of polyethyleneimine (PEI) (Polysciences) and 0.5 µg DNA per mL HEK293 culture. The ratio applied for heavy chain and light chain was 1 to 3. 4 h after transfecting the cells, 10% of the total culture volume of 9% Primatone HS/UF (Kerry BioScience/Sheffield) was added. The cultures were incubated for 6 d shaking at 100 rpm and afterwards harvested by centrifugation at 1.000×g for 10 min. 10 µL of a 50%-slurry of Protein A-Sepharose beads (GE Healthcare) in 1×PBS were added per mL of supernatant of the cell cultures. The supernatant containing the beads was incubated for at least 2 h on a rotor at 25 rpm, 4° C. Beads were pelleted by centrifugation at 610×g for 2 min with reduced deceleration speed. The beads with the bound functional mABs were transferred to a 96 well 0.45 µm filter plate (PALL) and consecutively washed with 1×PBS, 1×PBS containing 0.5 M NaCl (ChemLab) and 0.5×PBS containing 0.15 M NaCl (ChemLab), each time applying the vacuum in between washing steps. The bound mABs were eluted using 50 mM sodium citrate (Sigma-Aldrich) containing 0.3 M NaCl (ChemLab) at pH 3. Eluted fractions were neutralized with 1M KHPO$_4$/KH$_2$PO$_4$ (VWR) at pH 8 and protein concentrations were measured in NanoDrop 2000 (Thermo Scientific). The screening was done either by Biacore, or using the MSD platform.

For screening by Biacore, several setups can be used. In a "direct" setup the binding of the purified antibody to the coated antigen on a CM5 chips (GE Healthcare) was measured at pH 7.4 or pH5.5 according to manufacturer's instructions at 25° C. in HBSEP buffer (0.01 M 4-(2-Hydroxyethyl)-1-piperazineethanesulfonic acid (HEPES) pH 7.4, 0.15 M NaCl (ChemLab), 3 mM EDTA, 0.005% (v/v) Surfactant P20) at pH 7.4 or using the same buffer but adjusted to pH 5.5 by adding 1 M HCl. In a different "capture" setup, the mutated antibody is capture on a Chip is coated with a polyclonal anti human IgG in all channels. mABs are injected in HBSEP to reach an RU of 150-300, followed by the injection of ligand (analyte) at varying concentration in HBSEP buffer at pH 7.4 or adjusted pH at 5.5. After each cycle, regeneration of the chip surface was done by 10 s injection of 10 mM glycine at pH 1.5. All kinetic analyses were done using appropriate software provided by GE Healthcare.

For the testing of the antibodies using the MSD platform, plate (MSD) was coated O/N with the target in 1×PBS at 4° C. The plate are then washed 3× with 200 µL of 1×PBS blocked with 150 µL of 1×PBS with 1% (m/v) Casein (Sigma-Aldrich) for 1-2 h at RT, shaking at 600 rpm. The plate is then washed 3× with 200 µL of 1×PBS containing 0.05% (m/v) Tween (Merck) (pH 7.4) or citrate buffer (0.05 M citric acid (Sigma-Aldrich), 0.14 M sodium citrate (Sigma-Aldrich), 0.15 M NaCl (ChemLab)) containing 0.05% (m/v) Tween (Merck) (pH 5.5). To calculate the dose response curves, 25 µL of mABs was added at various concentrations is added to the wells at pH 7.4 or pH 5.5 in 1×PBST (PBS containing 0.05 (m/v) Tween) (pH 7.4) or citrate buffer containing 0.05% (m/v) Tween (Merck) (pH 5.5). After 1 h at incubation at RT, shaking at 600 rpm. The wells are washed 4× with 1×PBST at pH 7.4 or pH 5.5. For the last washing step, an extra incubation of 5-10 min at RT, shaking at 600 rpm, with PBST pH 7.4 or citrate buffer pH 5.5 was performed. All wells were finally washed with 1×PBS (pH 7.4) and 25 µL of 1:2000 Goat anti human Fc Sulfo (MSD) in 0.1% Casein (Sigma-Aldrich)-1×PBS (pH 7.4) was added for 1 h at RT, shaking at 600 rpm. After washing steps with 200 µL 1×PBST (pH 7.4), 150 µL of MSD reading buffer (MSD) was added to each well and the plate was read in QuickPlex SQ 120 machine (MSD).

In addition to the single pH setup (antibody binding and washing at the same pH of 7.4 or 5.5), we also tested a dual pH ELISA where the antibody binding is done at pH 7.4 but the washing is done in citrate buffer at pH 5.5. This setup allows discrimination between an effect of the pH on the association or dissociation or both, and is more representative of the in vivo situation where binding occurs at pH 7.4 and release of the antigen must occur in the endosome at pH 5.5-6.0.

After screening all the single mutants indicated in Table 2, several single mutants appeared to have an effect on the pH dependent binding (table 3). 5D1VLm3, 5D1VHm6, 5D1VHm14 for example had a significant pH dependent binding as compared to the 5D1 wt. in addition 5D1VHm13 had some improved pH dependency with advantageous kinetics.

TABLE 3

| | pH buffer | kd (1/s) | KD (M) | Ratio kd | Ratio KD |
|---|---|---|---|---|---|
| mAb exp#1 | | | | | |
| 5D1wt | 7.4 | 8.9E−04 | 6.1E−10 | 1.33 | 1.15 |
| | 5.5 | 1.2E−03 | 7.0E−10 | | |
| 5D1VHm6 | 7.4 | 2.9E−03 | 2.4E−09 | 10.07 | 1.69 |
| | 5.5 | 3.0E−02 | 4.0E−09 | | |
| 5D1VLm3 | 7.4 | 1.3E−03 | 1.4E−09 | 25.74 | 3.07 |
| | 5.5 | 3.3E−02 | 4.2E−09 | | |
| mAb exp#2 | | | | | |
| 5D1wt | 7.4 | 8.7E−04 | 6.8E−10 | 2.38 | 2.19 |
| | 5.5 | 2.1E−03 | 1.5E−09 | | |
| 5D1VHm5 | 7.4 | 2.6E−03 | 1.5E−09 | 3.53 | 8.05 |
| | 5.5 | 9.1E−03 | 1.2E−08 | | |
| 5D1VHm6 | 7.4 | 3.4E−03 | 2.9E−09 | 9.63 | 2.98 |
| | 5.5 | 3.2E−02 | 8.6E−09 | | |
| 5D1VHm10 | 7.4 | 1.3E−03 | 1.7E−09 | 1.59 | 11.91 |
| | 5.5 | 2.0E−03 | 2.0E−08 | | |

TABLE 3-continued

| | pH buffer | kd (1/s) | KD (M) | Ratio kd | Ratio KD |
|---|---|---|---|---|---|
| 5D1VHm13 | 7.4 | 3.9E−04 | 3.8E−10 | 2.57 | 2.21 |
| | 5.5 | 1.0E−03 | 8.3E−10 | | |
| 5D1VHm14 | 7.4 | 9.1E−04 | 1.0E−09 | 3.72 | 34.76 |
| | 5.5 | 3.4E−03 | 3.6E−08 | | |
| 5D1VLm1 | 7.4 | 7.7E−04 | 6.1E−10 | 2.16 | 3.38 |
| | 5.5 | 1.7E−03 | 2.1E−09 | | |

Figure 2:
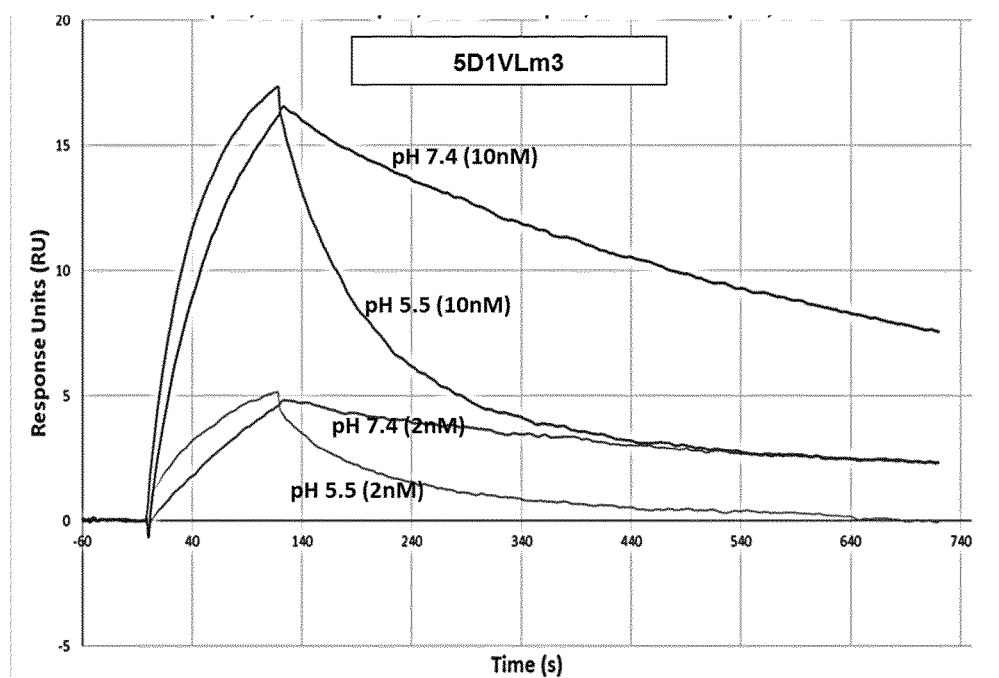
FIGS. 2, 3 and 4: illustrate pH dependent binding of histidine mutants of parental antibody 5D1, as measured using the MSD technique.
Figure 3:
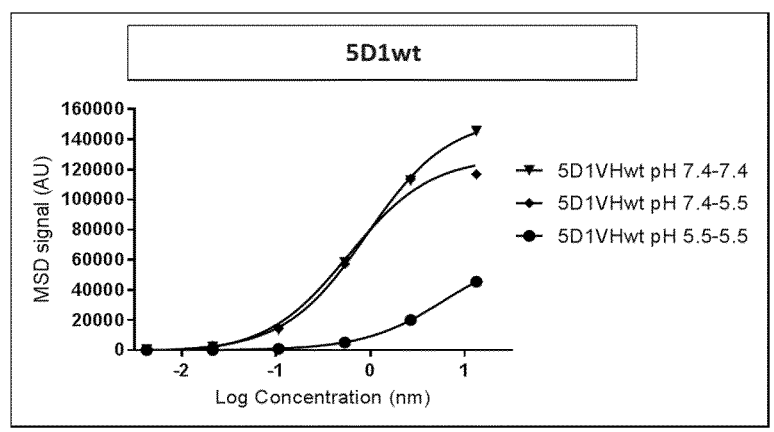
Figure 3:
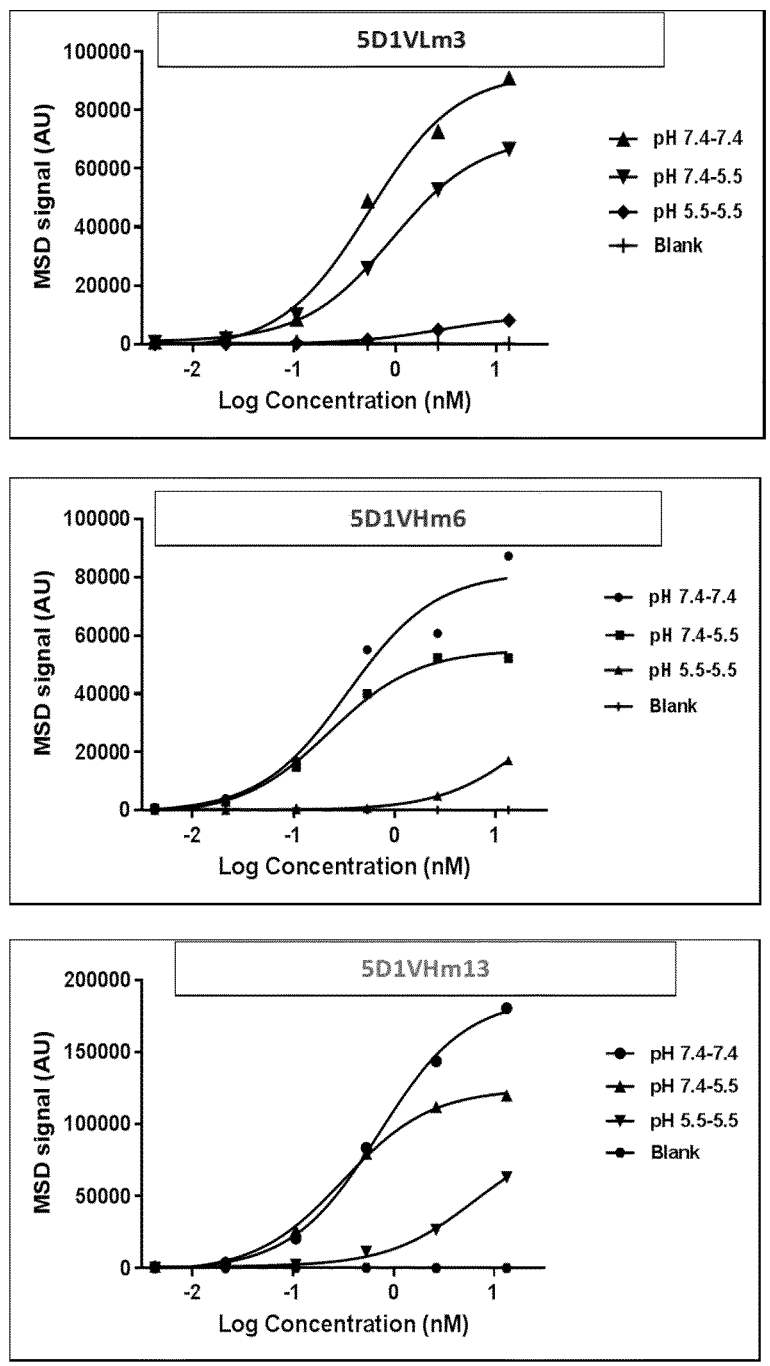
Figure 4:
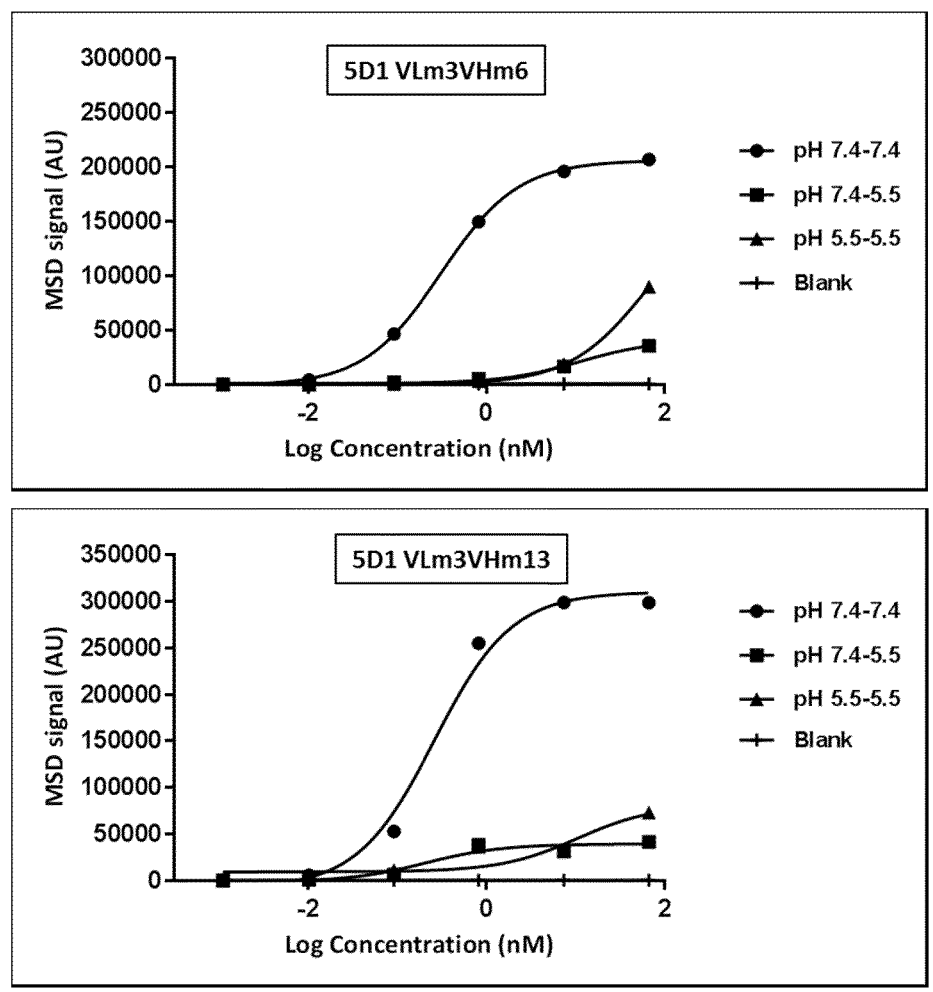

The pH dependency was also observed using the MSD technology, as shown in FIGS. 2 and 3, and Table 4. The effect of these mutations is visible on the curves shown in FIG. 2, where pH 5.5 is applied during washing (max binding is decreased) and both at binding and washing (most binding is lost for mutant 5D1VLm3 and 5D1VHm6) whilst the EC50 measured at pH 7.4 remains similar to the wild type parental antibody.

TABLE 4

| | EC50 (nM) | | |
|---|---|---|---|
| | pH 7.4-7.4 | pH 7.4-5.5 | pH 5.5-5.5 |
| 5D1 wt | 0.91 | 0.58 | nd |
| 5D1VLm3 | 0.56 | 0.93 | nd |
| 5D1VHm6 | 0.34 | 0.23 | nd |
| 5D1VHm13 | 0.71 | 0.31 | nd |

These data suggest that although pH dependency has been introduced, the effect is more significant on the association phase than on the dissociation. Therefore, it may be beneficial to introduce further histidine mutations in order to enhance pH dependency.

EXAMPLE: 4 COMBINING HISTIDINE MUTATIONS TO FURTHER INCREASE PH DEPENDENCY

Because VLm3, VHm6 and VHm13 all had an effect on the pH dependency, these mutations were combined within the same antibody. The double HIS mutants VLm3/VHm6 and VLm3/VHm13 were made simply by combining the plasmid encoding for each of the chain together during the transfection of the HEK293 cells. The pH dependency of the resulting antibodies was tested in MSD (see FIG. 4).

Combination of the mutations had a very positive effect on the pH dependency, as shown in Table 5. The double mutants showed very poor binding at pH 5.5 (pH5.5-pH5.5 setup). In contrast, most antibody bound at pH 7.4 was released during the pH 5.5 wash (pH7.4-pH 5.5 setup).

TABLE 5

| EC50(nM) | pH7.4-7.4 | pH7.4-5.5 | pH5.5-5.5 |
|---|---|---|---|
| 5D1 | 0.16 | 0.11 | 0.19 |
| 5D1 VLm3/VHm6 | 0.31 | 11.12 | nd |
| 5D1 VLm3/VHm13 | 0.26 | nd | nd | nd: EC50 not measurable due to low binding

EXAMPLE: 5 FULL MUTATION ANALYSIS USING THE HEAT MAP TO INCREASE PH DEPENDENCY OF ANTIBODY 3D6

The pH dependency of antibody 3D6 directed against the second antigen target was introduced using the heat map. According to the heat map and CDR length, 25 positions were amenable for histidine replacement in the VH of 3D6 and 16 in the Vkappa of 3D6 (see table 6). 21 of these 25 positions were tested in an initial screen.

TABLE 6

| VH3D6 | VH3-23 | | VK3D6 | VK1-39 | |
|---|---|---|---|---|---|
| VH3D6m1 | 31 | CDR1 | VK3D6m1 | 27 | CDR1 |
| not tested | 32 | | not tested | 27d | |
| VH3D6m18 | 33 | | not tested | 29 | |
| VH3D6m2 | 35 | | VK3D6m2 | 31 | |
| VH3D6m19 | 50 | CDR2 | VK3D6m3 | 32 | |
| VH3D6m3 | 52 | | VK3D6m4 | 53 | CDR2 |
| VH3D6m4 | 52a | | VK3D6m5 | 54 | |
| VH3D6m20 | 53 | | VK3D6m6 | 55 | |
| VH3D6m5 | 56 | | VK3D6m7 | 89 | CDR3 |
| VH3D6m6 | 58 | | VK3D6m8 | 90 | |
| not tested | 59 | | VK3D6m9 | 91 | |
| VH3D6m7 | 62 | | VK3D6m10 | 92 | |
| not tested | 63 | | VK3D6m11 | 93 | |
| VH3D6m8 | 95 | CDR3 | VK3D6m12 | 94 | |
| VH3D6m9 | 96 | | VK3D6m13 | 95 | |
| VH3D6m10 | 97 | | VK3D6m14 | 96 | |
| VH3D6m11 | 98 | | VK3D6m15 | 97 | |
| VH3D6m12 | 99 | | | | |
| VH3D6m13 | 100 | | | | |
| VH3D6m14 | 100a | | | | |
| VH3D6m15 | 100b | | | | |
| VH3D6m16 | 100c | | | | |
| VH3D6m17 | 100d | | | | |
| VH3D6m21 | 101 | | | | |
| VH3D6m22 | 102 | | | | |

For each mutation, a synthetic gene was ordered (Geneart, Thermo Scientific), cloned in appropriate expression vector and antibody was produced as indicated in example 3. The pH dependency of the antibodies was tested in a capture setup, where a Biacore T200 chip was coated with high amount of an anti-human Fc antibody (8000 RU). Then, the 3D6 antibody wild type or mutants were injected (2 μg/ml) in HBS-EP pH 7.4 to reach preferably 100-200RU. After stabilization of the signal, the target was injected at 2.5 or 10 nM and washed using an HBS-EP buffer at pH 7.4 or 5.5. The equilibrium dissociation constant KD (M) at pH 7.4 was measured using the T200 software. Only the dissociation constant (kd 1/s) was extracted from the fitting at pH 5.5, since the association was done at pH 7.4. The results are presented in table 7 and 8.

TABLE 7

| | | Washing at pH 7.4 | | | | Washing at pH 5.5 | | | pH |
| --- | --- | --- | --- | --- | --- | --- | --- | --- | --- |
| | | ka (1/Ms) | kd (1/s) | KD (M) | Rmax (RU) | Chi$^2$ (RU$^2$) | kd (1/s) | Rmax (RU) | Chi$^2$ (RU$^2$) | Ratio kd |
| | 3D6VHwt | 7.3E+05 | 3.7E−04 | 5.1E−10 | 21 | 0.037 | 6.7E−04 | 24 | 0.051 | 1.8 |
| CDR1 | 3D6VHm1 | 5.2E+05 | 4.8E−04 | 9.2E−10 | 19 | 0.036 | 7.3E−04 | 24 | 0.170 | 1.5 |
| CDR1 | 3D6VHm18 | 5.9E+05 | 2.8E−04 | 4.7E−10 | 26 | 0.026 | 4.2E−04 | 27 | 0.223 | 1.5 |
| CDR1 | 3D6VHm2 | 6.0E+05 | 8.6E−04 | 1.4E−09 | 23 | 0.012 | 1.4E−03 | 28 | 0.128 | 1.6 |
| CDR2 | 3D6VHm19 | 7.6E+05 | 5.8E−04 | 7.6E−10 | 24 | 0.021 | 6.8E−04 | 25 | 0.072 | 1.2 |
| CDR2 | 3D6VHm3 | no binding | | | | | no binding | | | |
| CDR2 | 3D6VHm4 | 8.1E+05 | 2.0E−03 | 2.4E−09 | 25 | 0.041 | 5.9E−04 | 26 | 0.060 | 0.3 |
| CDR2 | 3D6VHm20 | 3.5E+05 | 5.8E−04 | 1.7E−09 | 13 | 0.013 | 6.6E−04 | 12 | 0.064 | 1.1 |
| CDR2 | 3D6VHm5 | 2.5E+06 | 1.3E−02 | 5.3E−09 | 8 | 0.142 | 1.5E+01 | 11 | 0.214 | 1122 |
| CDR2 | 3D6VHm6* | no binding | | | | | 7.0E−04 | 7 | 0.040 | |
| CDR2 | 3D6VHm7 | 6.0E+05 | 4.6E−04 | 7.7E−10 | 25 | 0.019 | 5.9E−04 | 26 | 0.097 | 1.3 |
| CDR3 | 3D6VHm8 | no binding | | | | | no binding | | | |
| CDR3 | 3D6VHm9 | 7.6E+05 | 1.7E−04 | 2.3E−10 | 25 | 0.025 | 4.0E−04 | 29 | 0.085 | 2.3 |
| CDR3 | 3D6VHm10 | 5.3E+05 | 2.3E−03 | 4.3E−09 | 14 | 0.052 | 1.6E+02 | 14 | 0.141 | 69432 |
| CDR3 | 3D6VHm11 | 4.6E+05 | 1.6E−03 | 3.5E−09 | 20 | 0.029 | 8.5E+01 | 20 | 0.310 | 53375 |
| CDR3 | 3D6VHm12 | no binding | | | | | no binding | | | |
| CDR3 | 3D6VHm13 | 1.2E+06 | 1.6E−03 | 1.3E−09 | 24 | 0.033 | 1.2E+02 | 33 | 0.711 | 78710 |
| CDR3 | 3D6VHm14 | no binding | | | | | no binding | | | |
| CDR3 | 3D6VHm15 | no binding | | | | | no binding | | | |
| CDR3 | 3D6VHm16 | 9.2E+05 | 3.7E−04 | 4.0E−10 | 35 | 0.083 | 1.4E−03 | 38 | 0.276 | 3.7 |
| CDR3 | 3D6VHm17 | 3.6E+05 | 4.1E−04 | 1.2E−09 | 12 | 0.025 | 6.3E−04 | 15 | 0.106 | 1.5 |
| CDR3 | 3D6VHm21 | 5.6E+05 | 2.6E−04 | 4.6E−10 | 25 | 0.021 | 3.7E−04 | 26 | 0.128 | 1.5 |
| CDR3 | 3D6VHm22 | 6.4E+05 | 3.4E−04 | 5.3E−10 | 25 | 0.023 | 4.7E−04 | 26 | 0.104 | 1.4 |
| | irrelevant | no binding | | | | | no binding | | | |

TABLE 8

| | | pH 7.4 | | | | | pH 5.5 | | | |
| --- | --- | --- | --- | --- | --- | --- | --- | --- | --- | --- |
| | | ka (1/Ms) | kd (1/s) | KD (M) | Rmax (RU) | Chi$^2$ (RU$^2$) | kd (1/s) | Rmax (RU) | Chi$^2$ (RU$^2$) | Ratio kd |
| | 3D6VKwt | 1.3E+06 | 4.7E−04 | 3.5E−10 | 22.4 | 0.254 | 7.2E−04 | 24.9 | 0.423 | 1.5 |
| | 3D6VKwt | 1.3E+06 | 4.6E−04 | 3.4E−10 | 22.6 | 0.275 | 7.0E−04 | 25.0 | 0.429 | 1.5 |
| CDR1 | 3D6VKm1 | 1.3E+06 | 4.9E−04 | 3.7E−10 | 20.5 | 0.207 | 1.0E−03 | 25.1 | 0.495 | 2.1 |
| CDR1 | 3D6VKm2 | 1.2E+06 | 4.1E−04 | 3.4E−10 | 22.1 | 0.252 | 1.3E−03 | 29.0 | 0.883 | 3.3 |
| CDR1 | 3D6VKm3 | 1.7E+06 | 1.5E−03 | 8.4E−10 | 22.1 | 0.182 | 1.6E−03 | 24.8 | 0.386 | 1.1 |
| CDR2 | 3D6VKm4 | 1.4E+06 | 4.1E−04 | 3.0E−10 | 21.7 | 0.266 | 9.5E−04 | 24.7 | 0.467 | 2.3 |
| CDR2 | 3D6VKm5 | 1.3E+06 | 3.5E−04 | 2.8E−10 | 24.2 | 0.356 | 1.1E−03 | 27.9 | 0.747 | 3.3 |
| CDR3 | 3D6VKm7 | 1.5E+06 | 5.5E−04 | 3.7E−10 | 26.0 | 0.379 | 1.4E−03 | 29.3 | 0.677 | 2.5 |
| CDR3 | 3D6VKm8 | 1.6E+06 | 1.0E−03 | 6.4E−10 | 20.0 | 0.196 | 1.1E−03 | 22.4 | 0.293 | 1.0 |
| CDR3 | 3D6VKm9 | 1.3E+06 | 2.4E−04 | 1.8E−10 | 28.1 | 0.439 | 5.8E−04 | 32.0 | 0.826 | 2.4 |
| CDR3 | 3D6VKm10 | 1.6E+06 | 9.8E−04 | 6.3E−10 | 21.2 | 0.222 | 1.8E−03 | 24.9 | 0.483 | 1.9 |
| CDR3 | 3D6VKm11 | 1.5E+06 | 1.0E−03 | 7.1E−10 | 22.3 | 0.256 | 1.2E−02 | 26.9 | 0.959 | 11.8 |
| CDR3 | 3D6VKm12 | 2.2E+06 | 2.1E−03 | 9.4E−10 | 6.2 | 0.101 | 1.7E−03 | 7.5 | 0.163 | 0.8 |
| CDR3 | 3D6VKm13 | 1.4E+06 | 7.9E−04 | 5.8E−10 | 4.2 | 0.021 | 9.9E−04 | 5.3 | 0.151 | 1.3 |
| CDR3 | 3D6VKm14 | no binding | | | | | no binding | | | |
| CDR3 | 3D6VKm15 | 1.6E+06 | 1.7E−03 | 1.1E−09 | 17.0 | 0.140 | 3.5E−03 | 19.4 | 0.314 | 2.0 |
| | IRRELEVANT | no binding | | | | | no binding | | | |

These data indicate that pH dependency has been introduced in 3D6 with minimal loss of binding at pH 7.4. It may be beneficial to combine the single histidine mutations in order to enhance pH dependency.

EXAMPLE: 6 COMBINING HISTIDINE MUTATIONS TO FURTHER INCREASE PH DEPENDENCY IN ANTIBODY 3D6

Based on the results in table 7 and 8, mutations introducing significant pH dependency and/or improving binding at pH 7.4 were combined with in the same domain, generating new mutant VHm23, VHm24, VHm25, VHm26, VKm16, VKm17, VKm18 and VKm19 (table 9). For example, 3D6VHm23 had mutation VHm9 and VHm13, 3D6VHm24 had mutation VHm0 and VHm16, etc. . . .

TABLE 9

| | VHm9 | VHm13 | VHm16 | | VKm5 | VKm9 | VKm11 |
|---|---|---|---|---|---|---|---|
| 3D6VHm23 | X | X | | 3D6VKm16 | X | X | |
| 3D6VHm24 | X | | X | 3D6VKm17 | X | | X |
| 3D6VHm25 | | X | X | 3D6VKm18 | | X | X |
| 3D6VHm26 | X | X | X | 3D6VKm19 | X | X | X |

The new VH and VK mutants were further combined with each other simply by combining the plasmid encoding for each of the chain together during the transfection of the HEK293 cells. For example, the antibody 3D6VHm23/VKm11 was done by co-transfecting the VHm23 mutant DNA with the mutant VKm11 DNA. After purification, the pH dependency of the resulting antibodies was tested using Biacore®, as described in example 5. The antibodies with good pH dependency and with a good affinity at pH 7.4 were further characterized with the only difference that a higher concentration of the target was added (0.04 nM; 0.1 nM; 0.37 nM; 1.1 nM; 3.3 nM and 10 nM). The KD (M) at pH 7.4 was measured using the T200 software. Only the dissociation constant (kd s−1) was extracted from the fitting at pH 5.5. The top 5 antibodies are indicated in table 10.

TABLE 10

| | pH diss | kd (1/s) | KD (M) | Rmax (RU) | kd diff |
|---|---|---|---|---|---|
| 3D6wt(old) | 7.4 | 2.4E−04 | 3.9E−10 | 46 | 2.7 |
| | 5.5 | 6.5E−04 | nt | 47 | |
| 3D6VHm23/VKm11 | 7.4 | 3.3E−04 | 5.6E−10 | 55 | 151515 |
| | 5.5 | 5.0E+01 | nt | 85 | |
| 3D6VHm24/VKm11 | 7.4 | 3.0E−04 | 5.2E−10 | 51 | 15.3 |
| | 5.5 | 4.6E−03 | nt | 62 | |
| 3D6VHm25/VKm5 | 7.4 | 2.8E−04 | 4.7E−10 | 60 | 28.2 |
| | 5.5 | 7.9E−03 | nt | 74 | |
| 3D6VHm13/VKm16 | 7.4 | 4.4E−04 | 8.9E−10 | 55 | 13.4 |
| | 5.5 | 5.9E−03 | nt | 64 | |
| 3D6VHm16/VKm17 | 7.4 | 6.0E−04 | 8.5E−10 | 57 | 166667 |
| | 5.5 | 1.0E+02 | nt | 68 | |

The results from the Biacore clearly show that the method presented here allowed the rapid identification of antibodies with great pH dependency with minimal loss of binding at pH 7.4

The invention claimed is:

1. A method of preparing an engineered antibody exhibiting pH-dependent binding to its antigen, comprising the steps of:

(a) preparing a panel of engineered variants of a parental antibody which binds to antigen, wherein each of the engineered variants in the panel differs from the parental antibody by substitution of at least one hot-spot amino acid residue with a histidine residue, wherein the at least one hot-spot amino acid residue is selected from the following hot-spot list:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 | wherein each of the engineered variants in the panel comprises an Fc region;

(b) screening the panel of engineered variants for pH dependent binding to the antigen and thereby identifying an engineered antibody exhibiting pH-dependent binding to the antigen.

2. The method of claim 1, wherein the engineered antibody identified in part (b) has lower affinity for its antigen at acidic pH than at neutral pH.

3. A method of preparing an engineered antibody exhibiting pH dependent binding to its antigen, comprising the steps of:

(a) preparing a panel of engineered variants of a parental antibody which binds to an antigen, wherein each of the engineered variants in the panel differs from the parental antibody by substitution of at least one hot-spot amino acid residue with a histidine residue, wherein the at least one hot-spot amino acid residue is selected from the following hot-spot list:

| | |
|---|---|
| VH CDR1 | H31, H32, H33, H35 |
| VH CDR2 | H50, H52, H52a, H53, H56, H58, H59, H62, H63 |
| VH CDR3 | H95, H96, H97, H98, H99, H100, H100a, H100b, H100c, H100d, H100e, H100f, H100h, H100i, H100j, H100l, H101, H102 |
| VL CDR1 | L27, L27d, L29, L30, L31, L32, L34 |
| VL CDR2 | L51, L52, L53, L54, L55 |
| VL CDR3 | L89, L90, L91, L92, L93, L94, L95a, L95b, L95c, L96 |
| FR | L49, L87 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n |
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 | wherein each of the engineered variants in the panel comprises an Fc region;
(b) screening the panel of engineered variants for pH dependent binding to the target antigen and thereby identifying selected amino acid positions at which the presence of histidine confers pH dependent binding to the antigen;
(c) preparing one or more further engineered variants of the parental antibody, wherein each of the variants comprises histidine at two or more selected amino acid positions identified in step (b), wherein each of the engineered variants in the panel comprises an Fc region; and
(d) screening the further engineered variants for pH dependent binding to the antigen; and thereby identifying an engineered antibody exhibiting pH dependent binding to the antigen.

4. The method of claim 3, wherein the engineered antibody identified in part (d) has lower affinity for its antigen at acidic pH than at neutral pH.

5. A method of preparing an engineered antibody exhibiting pH dependent binding to its antigen, comprising the steps of:
(a) preparing a first panel of engineered variants of a parental antibody which binds to an antigen, wherein each of the engineered variants in the panel differs from the parental antibody by substitution of at least one hot-spot amino acid residue in the VH domain with a histidine residue, wherein the at least one hot-spot amino acid residue is selected from the following hot-spot list:

| | |
|---|---|
| VH CDR1 | H31, H32, H33, H35, |
| VH CDR2 | H50, H52, H52a, H53, H56, H58, H59, H62, H63, |
| VH CDR3 | H95, H96, H97, H98, H99, H100, H100a, H100b, H100c, H100d, H100e, H100f, H100h, H100i, H100j, H100l, H101, H102 | and at least one amino acid residue from the following cold-spot list is not substituted with histidine:

| | |
|---|---|
| VH CDR1 | H34, H35a, H35b, H35c |
| VH CDR2 | H51, H52b, H52c, H54, H55, H57, H60, H61, H64, H65 |
| VH CDR3 | H100g, H100k, H100m, H100n | wherein each of the engineered variants in first the panel comprises an Fc region;
(b) screening the first panel of engineered variants for pH dependent binding to the antigen; and thereby identifying one or more selected amino acid positions in the VH domain at which the presence of histidine confers pH dependent binding;
(c) preparing a second panel of engineered variants of the parental antibody, wherein each of the engineered variants in the panel differs from the parental antibody by substitution of at least one hot-spot amino acid residue in the VL domain with a histidine residue, wherein the at least one hot-spot amino acid residue is selected from the following hot-spot list:

| | |
|---|---|
| VL CDR1 | L27, L27d, L29, L30, L31, L32, L34 |
| VL CDR2 | L51, L52, L53, L54, L55 |
| VLCDR3 | L89, L90, L91, L92, L93, L94, L95, L95a, L95b, L95c, L95d, L95e, L95f, L96, L97 | and at least one amino acid residue selected from the following cold-spot list is not substituted with histidine:

| | |
|---|---|
| VL CDR1 | L24, L25, L26, L27a, L27b, L27c, L27e, L28, L33 |
| VL CDR2 | L50, L51a, L51b, L51c, L51d, L56 |
| VL CDR3 | L95, L95d, L95e, L95f, L97 | wherein each of the engineered variants in the second panel comprises an Fc region;
(d) screening the second panel of engineered variants for pH dependent binding to the antigen; and thereby identifying one or more selected amino acid positions in the VL domain at which the presence of histidine confers pH dependent binding;
(e) preparing one or more further engineered variants of the parental antibody, wherein each of the variants differs from the parental antibody by substitution of the hot-spot amino acid at one or more of the selected amino acid positions in the VH domain identified in step (b) with histidine and by substitution of the hot-spot amino acid at one or more of the selected amino acid positions in the VL domain identified in step (d) with histidine, wherein each of the engineered variants comprises an Fc region; and
(f) screening the further engineered variants for pH dependent binding to the antigen, thereby identifying an engineered antibody exhibiting pH-dependent binding to the antigen.

6. The method of claim 5, wherein the engineered antibody identified in part (f) has lower affinity for its antigen at acidic pH than at neutral pH.

7. The method of claim 1, wherein:
(a) the dissociation rate constant ($k_d$) for the engineered antibody-antigen interaction at acidic pH is higher than the dissociation rate constant ($k_d$) for the engineered antibody-antigen interaction at neutral pH;
(b) the dissociation rate constant ($k_d$) for the engineered antibody-antigen interaction at acidic pH is higher than the dissociation rate constant ($k_d$) for the parental antibody-antigen interaction at acidic pH; and/or
(c) the equilibrium dissociation constant ($K_D$) for the engineered antibody-antigen interaction at acidic pH is higher than the equilibrium dissociation constant ($K_D$) for the engineered antibody-antigen interaction at neutral pH.

8. The method of claim 1, wherein at least two hot-spot amino acid residues are selected from the hot-spot list.

9. The method of claim 1, wherein at least three hot-spot amino acid residues are selected from the hot-spot list.

10. The method of claim 1, wherein at least four hot-spot amino acid residues are selected from the hot-spot list.

11. The method of claim 1, wherein one or more of the following residues is also substituted with histidine: H100g, H100k, H100m, H100n, L95, L95d, L95e, L95f, and L97.

12. The method of claim 1, wherein at least two amino acid residues selected from the cold-spot list are not substituted with histidine.

13. The method of claim 1, wherein at least three amino acid residues selected from the cold-spot list are not substituted with histidine.

14. The method of claim 1, wherein none of the amino acid residues selected from the cold-spot list for VHCDR1, VHCDR2, VLCDR1 and VLCDR2 are substituted with histidine.

15. The method of claim 1, wherein the parental antibody or the CDRs thereof are derived from a camelid species.

16. The method of claim 3, wherein:
   (a) the dissociation rate constant ($k_d$) for the engineered antibody-antigen interaction at acidic pH is higher than the dissociation rate constant ($k_d$) for the engineered antibody-antigen interaction at neutral pH;
   (b) the dissociation rate constant ($k_d$) for the engineered antibody-antigen interaction at acidic pH is higher than the dissociation rate constant ($k_d$) for the parental antibody-antigen interaction at acidic pH; and/or
   (c) the equilibrium dissociation constant ($K_D$) for the engineered antibody-antigen interaction at acidic pH is higher than the equilibrium dissociation constant ($K_D$) for the engineered antibody-antigen interaction at neutral pH.

17. The method of claim 3, wherein at least two hot-spot amino acid residues are selected from the hot-spot list.

18. The method of claim 3, wherein at least three hot-spot amino acid residues are selected from the hot-spot list.

19. The method of claim 3, wherein at least four hot-spot amino acid residues are selected from the hot-spot list.

20. The method of claim 3, wherein one or more of the following residues is also substituted with histidine: H100g, H100k, H100m, H100n, L95, L95d, L95e, L95f, and L97.

21. The method of claim 3, wherein at least two amino acid residues selected from the cold-spot list are not substituted with histidine.

22. The method of claim 3, wherein at least three amino acid residues selected from the cold-spot list are not substituted with histidine.

23. The method of claim 3, wherein none of the amino acid residues selected from the cold-spot list for VHCDR1, VHCDR2, VLCDR1 and VLCDR2 are substituted with histidine.

24. The method of claim 3, wherein the parental antibody or the CDRs thereof are derived from a camelid species.

25. The method of claim 5, wherein:
   (a) the dissociation rate constant ($k_d$) for the engineered antibody-antigen interaction at acidic pH is higher than the dissociation rate constant ($k_d$) for the engineered antibody-antigen interaction at neutral pH;
   (b) the dissociation rate constant ($k_d$) for the engineered antibody-antigen interaction at acidic pH is higher than the dissociation rate constant ($k_d$) for the parental antibody-antigen interaction at acidic pH; and/or
   (c) the equilibrium dissociation constant ($K_D$) for the engineered antibody-antigen interaction at acidic pH is higher than the equilibrium dissociation constant ($K_D$) for the engineered antibody-antigen interaction at neutral pH.

26. The method of claim 5, wherein at least two hot-spot amino acid residues are selected from the hot-spot list.

27. The method of claim 5, wherein at least three hot-spot amino acid residues are selected from the hot-spot list.

28. The method of claim 5, wherein at least four hot-spot amino acid residues are selected from the hot-spot list.

29. The method of claim 5, wherein one or more of the following residues is also substituted with histidine: H100g, H100k, H100m, H100n, L95, L95d, L95e, L95f, and L97.

30. The method of claim 5, wherein at least two amino acid residues selected from the cold-spot list are not substituted with histidine.

31. The method of claim 5, wherein at least three amino acid residues selected from the cold-spot list are not substituted with histidine.

32. The method of claim 5, wherein none of the amino acid residues selected from the cold-spot list for VHCDR1, VHCDR2, VLCDR1 and VLCDR2 are substituted with histidine.

33. The method of claim 5, wherein the parental antibody or the CDRs thereof are derived from a camelid species.

* * * * *